US007698155B1

(12) United States Patent
Prasad et al.

(10) Patent No.: US 7,698,155 B1
(45) Date of Patent: Apr. 13, 2010

(54) SYSTEM FOR DETERMINING A DISEASE CATEGORY PROBABILITY FOR A HEALTHCARE PLAN MEMBER

(75) Inventors: Badri N. Prasad, Escondido, CA (US); Gerald Lutgen, St. Paul, MN (US); Xingue Huang, Maple Grove, MN (US)

(73) Assignee: Ingenix, Inc., Eden Prairie, MN (US)

( * ) Notice: Subject to any disclaimer, the term of this patent is extended or adjusted under 35 U.S.C. 154(b) by 1967 days.

(21) Appl. No.: 10/310,017

(22) Filed: Dec. 4, 2002

Related U.S. Application Data

(60) Provisional application No. 60/429,869, filed on Nov. 29, 2002.

(51) Int. Cl.
*G06F 19/00* (2006.01)
*G06Q 40/00* (2006.01)

(52) U.S. Cl. ............................................. 705/3; 705/4

(58) Field of Classification Search ................... 705/2–3
See application file for complete search history.

(56) References Cited

U.S. PATENT DOCUMENTS

| | | | |
|---|---|---|---|
| 5,277,188 A * | 1/1994 | Selker | 600/508 |
| 5,404,292 A | 4/1995 | Hendrickson | |
| 5,544,044 A * | 8/1996 | Leatherman | 705/3 |
| 5,557,514 A | 9/1996 | Seare et al. | |
| 5,835,897 A | 11/1998 | Dang | |
| 5,956,689 A * | 9/1999 | Everhart, III | 705/3 |
| 5,970,463 A | 10/1999 | Cave et al. | |
| 5,976,082 A | 11/1999 | Wong et al. | |
| 6,000,828 A | 12/1999 | Leet | |
| 6,370,511 B1 | 4/2002 | Dang | |
| 6,578,003 B1 | 6/2003 | Camarada et al. | |
| 6,587,829 B1 | 7/2003 | Camarda et al. | |
| 2001/0020229 A1 | 9/2001 | Lash | |
| 2003/0167189 A1* | 9/2003 | Lutgen et al. | 705/3 |

OTHER PUBLICATIONS

Transamerica Reinsurance, Protective Value of Prescription Drug Data, http://www.transamericareinsurance.comImedia/media Feb. 4, 2009.*
"Protective Value of Prescription Drug Data", http://www.transamericareinsurance.com/media/media Feb. 4, 2009 (2pgs).
"Morality and Prescription Drug Use: An Analysis Using the CHS Limited Access Data", *Journal of Insurance Medicine*, APT Online Jan. 13, 2009 (2pgs).
"Prescription Data Used to Assess Consumers", http://www.washingtonpost.com/wp-dyn/content/article/2008/08/03/AR2008080302077 (4pgs).

* cited by examiner

*Primary Examiner*—C. Luke Gilligan
*Assistant Examiner*—Tran Nguyen
(74) *Attorney, Agent, or Firm*—Dorsey & Whitney LLP; Adriana S. Luedke

(57) ABSTRACT

A system and method is provided for determining a probability that a member of a health plan has a disease or condition within one or more disease categories, by using data from the member's pharmacy claims. Logistic regression models are generated for each condition category using therapeutic drug categories, provider information, and/or other variables including member demographic information.

12 Claims, 20 Drawing Sheets

Parallax Pharmacy Model
Application | Help

Normative Cost Distribution

| Disease Category | PMPM Dollars | Percent of Total PMPM |
|---|---|---|
| Pregnancy | 13.27 | 11% |
| Atherosclerotic coronary vascular disease and cardiac arrest | 5.15 | 4% |
| Other miscellaneous conditions | 4.17 | 3% |
| Affective disorders | 3.94 | 3% |
| Major traumatic injury | 3.71 | 3% |
| Upper respiratory infection | 3.61 | 3% |
| Disorders of the Spine | 3.33 | 3% |
| Neoplasms of the breast and female reproductive system | 3.26 | 3% |
| Other gastrointestinal disorders | 3.25 | 3% |
| Hypertension | 2.96 | 2% |

Record: 1 of 102

Click on any blue column heading to sort by that category    <<Back<<  |  >>Detail>>

FIG. 5

Disease Prevalence in the Population

| Disease Category | Predicted Member Count | Prevalence in Current Population | Prevalence Point Difference | Prevalence in Norm Population | Percent of Total Cost |
|---|---|---|---|---|---|
| Ache or unspecified arthropathies and minor tendon disorders | 24 | 3% | 0% | 3% | 1% |
| Affective disorders | 43 | 6% | -1% | 7% | 3% |
| Anemia, acquired | 4 | 1% | 0% | 0% | 0% |
| Anemia, congenital | 0 | 0% | 0% | 0% | 0% |
| Atherosclerotic coronary vascular disease and cardiac arrest | 8 | 1% | -1% | 2% | 1% |
| Carditis and cardiomyopathy/CHF | 2 | 0% | 0% | 1% | 0% |
| Congenital anomalies | 10 | 1% | 0% | 1% | 1% |
| Congenital or acquired central degenerative disorders | 3 | 0% | 0% | 1% | 0% |
| Crystalline arthritis | 4 | 1% | 0% | 1% | 0% |
| Degenerative joint disorders, other than spine | 16 | 2% | -1% | 3% | 1% |

Record: 1 of 102

Enter Total Cost for past year ($) to see amounts: 9,000,000    Show Total Cost as: ● Percent ○ Amount Click on a column heading to sort prevalence,
Right-click on a disease category to view classes, OR
Right-click on population prevalence to view members <<Back<<

Figure 12:
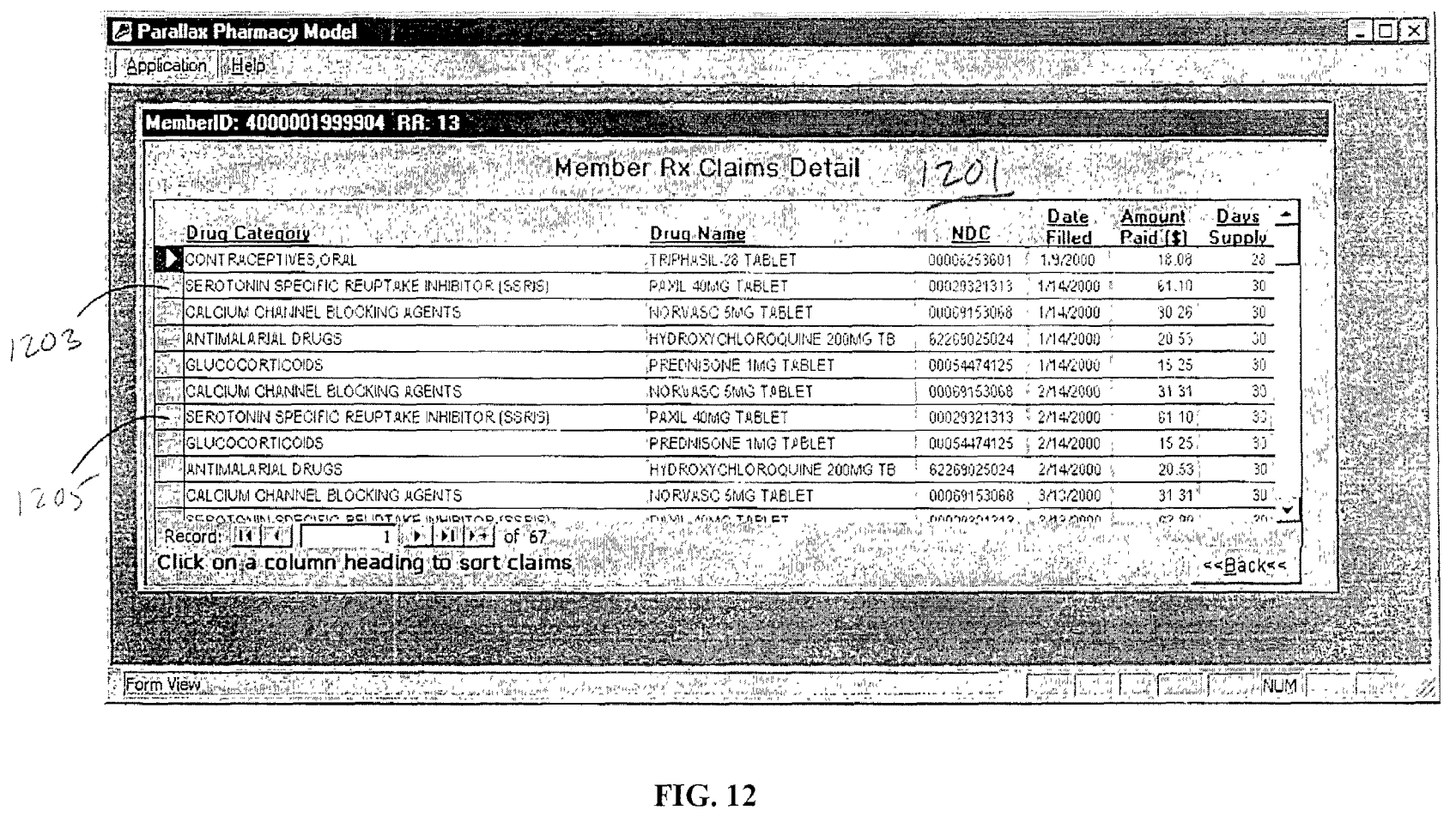

| Drug Category | Drug Name | NDC | Date Filled | Amount Paid ($) | Days Supply |
|---|---|---|---|---|---|
| CONTRACEPTIVES, ORAL | TRIPHASIL-28 TABLET | 00006253601 | 1/9/2000 | 18.08 | 28 |
| SEROTONIN SPECIFIC REUPTAKE INHIBITOR (SSRIS) | PAXIL 40MG TABLET | 00029321313 | 1/14/2000 | 61.10 | 30 |
| CALCIUM CHANNEL BLOCKING AGENTS | NORVASC 5MG TABLET | 00069153068 | 1/14/2000 | 30.26 | 30 |
| ANTIMALARIAL DRUGS | HYDROXYCHLOROQUINE 200MG TB | 62269025024 | 1/14/2000 | 20.55 | 30 |
| GLUCOCORTICOIDS | PREDNISONE 1MG TABLET | 00054474125 | 1/14/2000 | 15.25 | 30 |
| CALCIUM CHANNEL BLOCKING AGENTS | NORVASC 5MG TABLET | 00069153068 | 2/14/2000 | 31.31 | 30 |
| SEROTONIN SPECIFIC REUPTAKE INHIBITOR (SSRIS) | PAXIL 40MG TABLET | 00029321313 | 2/14/2000 | 61.10 | 30 |
| GLUCOCORTICOIDS | PREDNISONE 1MG TABLET | 00054474125 | 2/14/2000 | 15.25 | 30 |
| ANTIMALARIAL DRUGS | HYDROXYCHLOROQUINE 200MG TB | 62269025024 | 2/14/2000 | 20.53 | 30 |
| CALCIUM CHANNEL BLOCKING AGENTS | NORVASC 5MG TABLET | 00069153068 | 3/13/2000 | 31.31 | 30 |

| Disease Category | Driver Rank |
|---|---|
| Inactive disorders | 1 |
| Obstructive pulmonary diseases | 2 |
| Vasculitis and connective tissue disorders | 3 |
| Other upper respiratory disorders | 4 |
| Female fertility and infertility management | 5 |
| Hypertension | 6 |
| Other gynecologic disorders | 7 |
| Other psychiatric disorders | 8 |
| Other neoplasms | 9 |
| Upper respiratory infection | 10 |

Click on a column heading to sort disease drivers

US 7,698,155 B1

SYSTEM FOR DETERMINING A DISEASE CATEGORY PROBABILITY FOR A HEALTHCARE PLAN MEMBER

CROSS-REFERENCE TO RELATED APPLICATION

This patent application claims priority to U.S. Provisional Application No. 60/429,869, filed on Nov. 29, 2002, the subject matter of which is incorporated herewith by reference.

BACKGROUND OF THE INVENTION

For the past few decades, the predominant model of healthcare management used by most health care plans in the managed care industry has been one that focuses primarily on approving or denying coverage for medical procedures based upon specially developed criteria. This system has been subject to some criticism from doctors who feel that their treatment decisions should not be questioned, and from patients who feel that their health care plan places undue emphasis on financial consequences at the expense of sound medical care. Further, the current model employed by health care plans fails to place the appropriate amount of emphasis on providing proactive care for plan members.

Studies have shown that an emphasis on proactive care can improve a health care plan member's overall health and well-being. Proactive care can also reduce the overall expense to a health care plan by replacing expensive medical procedures and treatments with less expensive proactive care activities. One technique for identifying plan members having a need for proactive care services is through the use of a predictive model for health care utilization. An exemplary system for predicting health care utilization is disclosed in co-pending U.S. patent application Ser. No. 09/635,911, entitled "System and Method for Modeling of Health Care Utilization," by Gerald L. Lutgen et al., filed Aug. 10, 2000, now issued U.S. Pat. No. 7,44,291 on Oct. 28, 2008, which is hereby incorporated by reference in its entirety. Another example of such a system uses a predictive model in combination with an identification of a factor influencing a plan member's amenability to proactive care intervention. Such a system is disclosed in co-pending U.S. patent application Ser. No. 09/733,215, entitled "Method for High-Risk Member Identification," by Badri N. Prasad et al., filed Dec. 8, 2000, now issued as U.S. Pat. No. 7,640,175 on Dec. 29, 2009, which is hereby incorporated by reference in its entirety.

Furthermore, the techniques described above, for predicting utilization of health care resources and identifying plan members in need of proactive care services, can also be used by a health care plan or by a plan administrator to manage costs by adjusting premiums and predicting future needs of the member population.

When a member of a health care plan receives care from health care providers, information regarding the care received is provided to plan administrators in documents commonly referred to as claims. Predominantly, this information is provided in the following three types of claims: physician claims, facility claims, and pharmacy claims. These claims are the documents that are submitted to the health care plan by physicians, hospitals, and pharmacies to receive reimbursement for care provided to the plan member. These documents generally contain coded data that provides information regarding the care received by the plan member. These claims are processed by the health care plan, and where appropriate, payment is transmitted to the health care provider.

Analysis and identification of plan members amenable to proactive care intervention are performed using data from these claims. Typically data from all three claims is used in the analysis. Occasionally, a plan data administrator has access to only the pharmacy claims for the plan members. Accordingly, there is a need in the art for a method of performing modeling and analysis of plan members using only the data from pharmacy claims.

For purposes of this specification, the phrase "physician claim" is used to refer to any professional service claim submitted to a health plan (typically recorded on an HCFA-1500 form or its equivalent), and the phrase "facility claim" is used to refer to any facility claim (typically recorded on a UB92 form). The phrase "medical claim" is used to refer to both physician claims and facility claims. Finally, the phrase "pharmacy claim" is used to refer to any claim submitted by a pharmacy or durable medical goods provider. Medical claims generally include codes for diagnoses and procedures relating to the plan member. The reason for the visit is typically represented by an International Classification of Diseases ("ICD") code, currently in its ninth revision and thus commonly referred to as "ICD-9." The description of the service provided in a medical claim typically takes one of three formats, an ICD-9 procedure code, a Common Procedural Terminology ("CPT") code (promulgated by the American Medical Association), or a Health Care Procedural Code ("HCPC") (promulgated by the Health Care Financing Administration).

The following materials serve as background for the present application and provide further information on some of the classification systems discussed: Physician's Current Procedural Terminology, CPT 2003, specified by the American Medical Association; HCPCS 2003 Medicare's National Level II Codes, specified by CMS; Med-Index ICD9-CM Ninth Revision, specified by the World Health Organization ("WHO"), each of which is hereby incorporated by reference in its entirety.

BRIEF SUMMARY OF THE INVENTION

A system and method is provided for determining a probability that a plan member has a disease category using the member's pharmacy claims data. In one embodiment, logistic regression models are generated for each disease or condition category using pharmacological categories, provider information, and other variables including member demographic information. The probability that a subject has a condition or disease within a specified disease category is represented by the equation $$P(Dx) = f(Rx \text{ profile, provider profile, demographics}).$$

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The detailed description will refer to the following drawings, wherein like numerals refer to like elements, and wherein:

FIG. 5 is a screen shot for a normative cost distribution screen in an exemplary GUI, according to the present system and method;

FIG. 6 is a screen shot for a disease prevalence in the population screen in an exemplary GUI, according to the present system and method;

FIG. 10 is a screen shot for a member Rx compliance screen in an exemplary GUI, according to the present system and method;

FIG. 12 is a screen shot for a member Rx claims detail screen in an exemplary GUI, according to the present system and method;

FIG. 13 is a screen shot for a member disease drivers screen in an exemplary GUI, according to the present system and method;

DETAILED DESCRIPTION

Figure 1A:
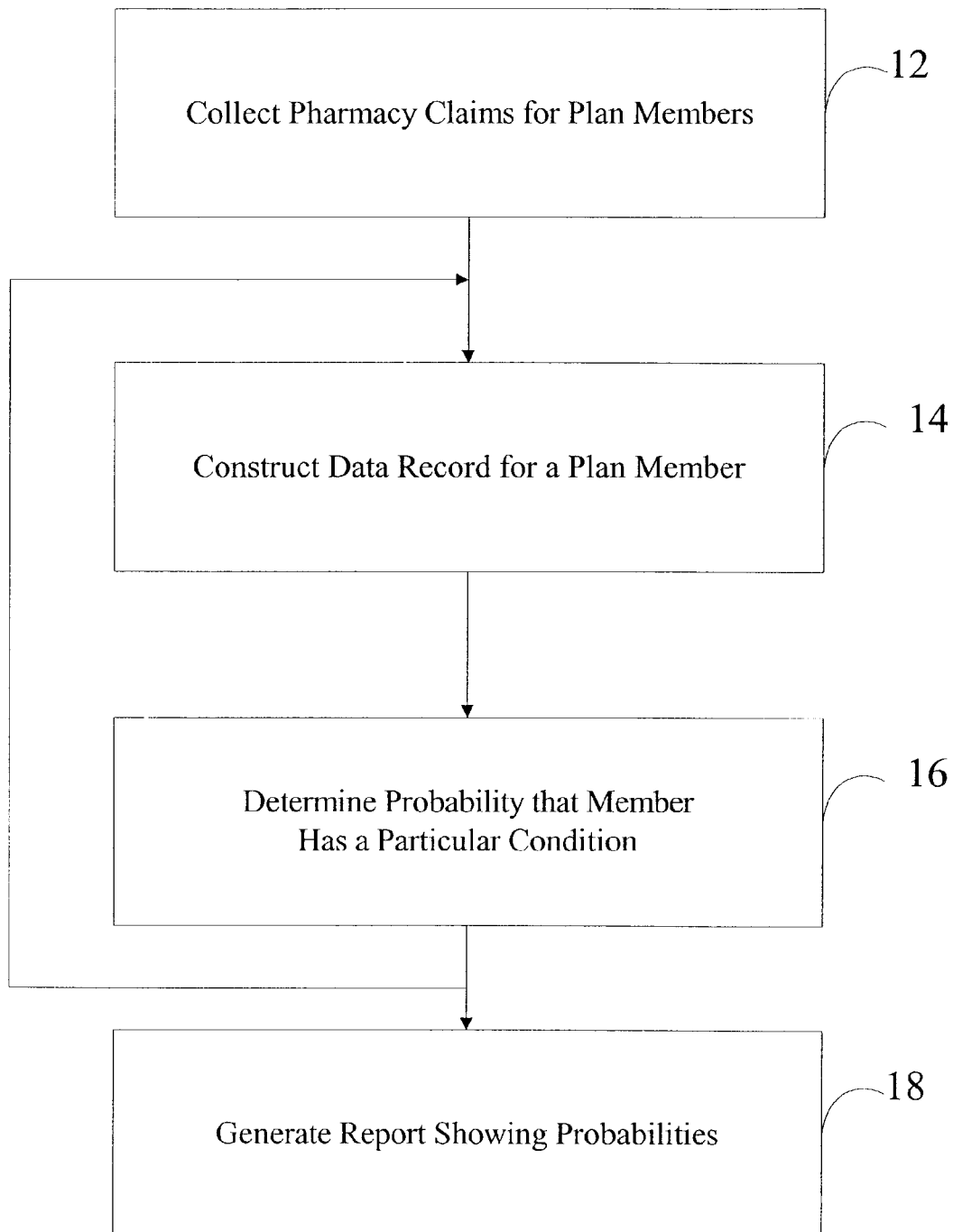
FIG. 1A is a flow diagram showing a method of determining whether a plan member has a specified disease or condition by analyzing the member's pharmacy claims, according to one embodiment of the present invention.

FIG. 1A is a flow diagram illustrating a modeling method 10 for analyzing pharmacy claims to determine probabilities that a plan member has certain medical conditions. As shown in FIG. 1A, the modeling method 10 includes collecting pharmacy claims (block 12), creating a standardized data record for the member (block 14), and determining a probability that the plan member has a particular disease or condition (block 16). In one embodiment, this determining step is repeated for each of several diseases or conditions. This process is repeated for each plan member. A report is then generated showing the results (block 18). In one embodiment, the modeling method 10 is repeated for each member of the plan. In one embodiment, the reporting step is not performed. For purposes of this application, 'plan member' refers to a person who is a member of a risk-bearing health care plan, which could include an employer self-insured plan.

The collection process (block 12), according to one embodiment, is performed on a computer by executing software to locate and transfer data from a central database (or multiple databases) or from a mass storage device. In another embodiment of the present invention, the collection process is performed manually by a person collecting hard copies of the necessary pharmacy claims and entering the data into a database.

Figure 1B:
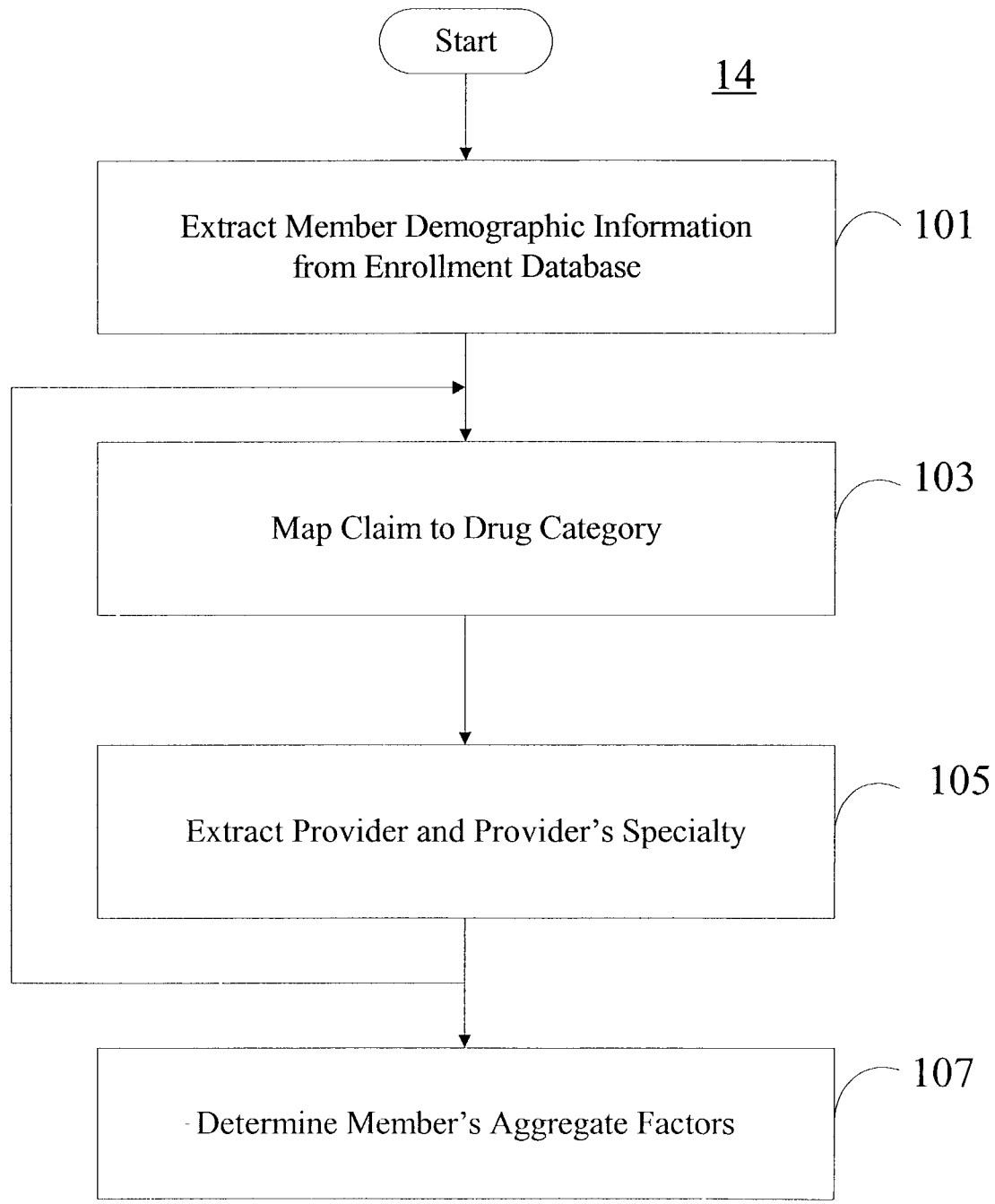
FIG. 1B is a flow diagram showing a method for extracting data from pharmacy claims (and other databases), which is necessary to determine a probability that a healthcare plan member has a disease or condition within a specified disease category, according to one embodiment of the present invention.

FIG. 1B is a flow diagram illustrating the standardized data record creation process 14 for extracting data from the pharmacy claims and other relevant databases. As shown in FIG. 1B, this record creation process 14 includes extracting member demographic information from a database (block 101), categorizing or mapping the pharmacy claim into a drug category (block 103), extracting the provider and the provider's specialty (block 105), repeating these steps for each pharmacy claim associated with the plan member, and determining aggregate factors for the plan member, such as number of unique drug categories, number of unique providers, and number of unique specialties (block 107).

In one embodiment, the member demographic information is extracted from a member enrollment database, which is typically kept for all members of a health care plan. In another embodiment, the member demographic information is extracted from the pharmacy claims. Member demographic information that may be extracted includes, for example, the member's age and the member's gender. Other demographic information (e.g., member's weight) may also be extracted at this step of the process.

A pharmacy claim typically specifies a drug category using a National Drug Code ("NDC"). To simplify the process of the present invention, the NDCs are placed into a reduced number of therapeutic drug classes or categories. Many types of therapeutic class definitions exist any of which can be used with the present invention. In one embodiment, for example, the NDCs are mapped into GC3 categories (also commonly referred to as HIC3 categories). The GC3 mapping process is a process known in the art (developed by First DataBank Inc.) for mapping the approximately 150,000 NDC codes for prescribed medications into about 600 related therapeutic categories. Any other method known in the art for mapping NDCs into therapeutic drug categories could also be used with the present invention. For purposes of convenience, the term "GC3" is used throughout the remainder of this specification, even though other systems could be used equally as well. Examples of GC3 categories are: anticonvulsants, beta blockers, leukotriene inhibitors, and distilled water.

The provider (i.e., prescriber or supplier) information is then determined for each claim. In one embodiment, the provider's specialty is extracted using a DEA identifier found in the pharmacy claim. This information is extracted from a database linking DEA numbers and physician demographics information. In another embodiment, this information is extracted from any other available database, as known to those skilled in the art, including a UPN database and a NABP database.

In one embodiment, other information is also extracted from each pharmacy claim for use with the method of the present invention. For example, in one embodiment, the days supply of the drug prescribed is extracted.

After each individual claim for a plan member has been analyzed, aggregate factors are determined. In one embodiment, claims for each member are analyzed to determine the number of unique providers, the number of unique provider specialties, and the number of unique GC3 drug categories prescribed. In other embodiments, other aggregate factors may be determined.

Once all of the pharmacy claims for a member have been analyzed, a record for the member is created. This record includes member demographic information, a dummy variable for each drug category (e.g., each GC3 category), a dummy variable for each provider specialty, and a number of unique providers. In one embodiment, the dummy variable for each drug category is a "1" if the member was prescribed a drug in the corresponding drug category and is a "0" if the member was not prescribed a drug in the corresponding drug category. Likewise, the dummy variable for each provider specialty is a "1" if the member received a prescription from a corresponding specialist and is a "0" if the member did not receive a prescription from a corresponding specialist. From this record, aggregate factors such as number of unique GC3 categories, number of unique providers, and number of unique provider specialties can be determined.

Once each member's claims have been analyzed and a record has been created for each member, modeling of the data can begin. During the model generation process, as further described below, data from this type of record, along with data from the physician and facility claims is used to generate a probability model for each condition of interest. In other words, to generate the models, a set of pharmacy, physician, and facility claims for some base period is used to determine which of the independent variables is an important indicator for each disease or condition of interest.

Before beginning the model generation process, the diseases or conditions of interest must be determined. The present invention will function effectively to develop models for any desired disease or disease category. A disease category, as discussed above, is a description of morbidity in a population more specific than organic specialty (e.g. cardiology, pulmonology). It is less specific than an individual condition label (e.g. diabetes type 1, asthma, depression). It is an appropriate level for describing the population morbidity. Examples of disease categories include diabetes, obstructive pulmonary diseases, and organic mental disorders.

In one embodiment, the specified disease categories are Clinical Care Groups ("CCGs"), which are further described below. Another embodiment of the invention is designed for operation with a Center for Medicare and Medicaid System ("CMS") defined set of disease categories. CMS is funded by the federal government and pays a health care plan to deliver health care services. The amount of the payment is based on the conditions in the members of the plan. In a CMS specification, the disease categories of interest are those disease categories that have been identified as forming the basis for the payments received by the health care plan.

Yet another embodiment of the invention is designed for assisting in life insurance underwriting. In this embodiment, the disease categories of interest are those indicative of or relevant to longevity or mortality of the member. For example, in a life insurance underwriting application, disease categories of interest may include congestive heart failure, smoking, HIV, cancer, and/or diabetes type I. A skilled artisan can readily envision other applications for the modeling methodology of the present invention, which would result in other disease categories of interest. Throughout the description of the modeling process, the phrase "disease category" or the abbreviation "Dx" will be used to represent a category of diseases or conditions, which have been predetermined based on the desired application of the models.

CCGs are an Ingenix innovation for classifying diagnosis codes on medical claims, into related categories. The CCG system is an aggregate description of the International Classification of Diseases (ICD) codes, procedure and drug codes inherent to managed care claims. The CCG system comes with a hierarchy of descriptions. At the lowest level is the Class (e.g. diabetes type I, diabetes type II, etc). At the intermediate level is the Category (e.g. diabetes, etc). At the highest level is the Specialty (e.g. endocrinology, cardiology, etc). Category is also referred to as disease category. The CCG system allows the over 14,000 ICD-9 codes to be placed into a more manageable number of CCG classes, namely about 460 related disease or diagnosis categories. These approximately 460 CCG classes can be further reduced into about 102 CCG categories. Finally, these approximately 102 CCG categories can be placed into about 20 CCG specialties. Each of these levels provides various advantages in analyzing the claims data. Some examples of CCG classes are: major depression with and without psychosis, ischemic heart disease, chronic hepatitis with and without complications, and pregnancy.

A medical episode grouper provides a more complete organization of medical events because it makes use of all available claims data while detecting important relationships between these claims. A medical episode grouper is described in greater detail in U.S. Pat. No. 6,223,164 B1 entitled, "Method and System for Generating Statistically-Based Medical Provider Utilization Profiles," assigned to Ingenix, the assignee of the present application, and is hereby incorporated by reference in its entirety. In one embodiment of the present invention, this medical episode grouper is used to categorize claims into CCGs. Those skilled in the art will recognize that alternative groupers could be used as the disease categories.

Generation of Probability Models

In generating the disease category probability models, the probability that a member has a disease category is represented by the equation:

$$P(Dx)=f(Rx \text{ profile, provider profile, demographics}). \qquad \text{(Eq. 1)}$$

In one embodiment, the disease categories are modeled using a statistical model, such as logistic regression. Logistic regression is a statistical modeling tool known to those skilled in the art for calculating the probability of certain events occurring. The probability models of the present invention return a mathematical probability. In one embodiment, a large membership for an entire calendar year is used to build the models. Pharmacy to disease modeling uses a subset of health plan member data that includes physician claims, facility claims, and pharmacy claims. In one embodiment, only members with full enrollment (i.e., 12-months) are included and used for the model generation. In another embodiment, claims from a 6-month enrollment period are used for model generation. In other embodiments, other sufficient claims time periods are used for model generation.

First, member level claims are processed by Ingenix's Clinical Care Groups to get member level CCG class information. After excluding the questionable and Rx only CCG episodes, and based on the relationship between CCG category and CCG class, a dummy (i.e., 0 or 1) variable is created based on CCG class information for each CCG category to indicate whether a member had a specific CCG category during the base calendar year. In one embodiment, a total of 102 dummy variables are generated corresponding to workable CCG categories.

In addition, NDC information from members' pharmacy claims data are used to generate a number of dummy variables to indicate whether a member had a pharmacy claim of a specific therapeutic class. The creation of the dummy variables is based on the relationship between NDC code and specific therapeutic class code. In one embodiment, for example the NDC code is mapped to a GC3 category. One dummy variable is generated for each therapeutic or drug class. For example, in an embodiment using GC3 categories, a total of around 600 dummy variables are generated for each of the around 600 therapeutic classes. In one embodiment, therapeutic classes that mainly represent orphan drugs, diagnostic agent, dietary supplement, food, wound healing agents, and implantable contraceptives are not used.

Moreover, based on provider information recorded on pharmacy claims, a number of dummy (0 or 1) variables are created to indicate whether a member had seen a provider specialist (e.g., a family physician, an endocrinologist, etc.). In one embodiment, a total of seventy-eight dummy variables are created to represent each of 78 different provider specialties. In addition, two numeric variables are created to represent the number of unique providers and number of provider specialties a member had seen during the time window.

Automation of Probability Modeling Process

In order to automate the modeling process, in one embodiment, one or more lookup tables are generated based on pharmacy and physician claims data, which act as a first-cut in determining which of the independent variables available in pharmacy claims is indicative of a disease category. One table, for example, captures the relationship (in terms of probability) between disease categories (e.g., CCG category) and the utilization of drugs of therapeutic classes (e.g., GC3). An exemplary table of this type is shown below for the disease category of HIV Infection.

| GC3 | DESCRIPTION | PROBABILITY(%) |
|---|---|---|
| G419 | W5B-ANTIVIRALS, HIV-SPECIFIC | 31.6 |
| G420 | W5C-ANTIVIRALS, HIV-SPECIFIC, PROTEASE INHIBITORS | 16.4 |
| G403 | W2A-ABSORBABLE SULFONAMIDES | 5.5 |
| G418 | W5A-ANTIVIRALS, GENERAL | 3.4 |

Another table captures the relationship (probability) between disease categories (CCG category) and provider specialties a member had seen during the time period. A randomly-pooled sample of member claims, in one embodiment, is used to create these look-up tables. The claims are processed through a medical episode grouper, as described above. For a given disease category, a probability is computed for each of the therapeutic classes. The probability is computed by dividing the number of members in the sample that have the disease category, and also were prescribed a drug in the therapeutic class, by the number of members having the disease category.

To use these tables as a first-cut in the modeling process, a threshold probability (e.g., one percent or any other appropriate threshold) is specified. Then, only those drug categories crossing the threshold probability for a specified disease category are included in the first model for that disease category. Likewise, only those physician specialties crossing the threshold probability for a specified disease category are included in the first model.

A number of logistic regressions are then conducted (using any system known in the art, such as the Statistical Analysis System available from SAS® Institute, Inc.), to generate mathematical models for each disease category. The general form of the functional equation of the model is:

$$\rho = \frac{\exp(b_0 + b_1 x_1 + \ldots + b_n x_n)}{(1 + \exp(b_0 + b_1 x_1 + \ldots + b_n x_n))} \quad \text{(Eq. 2)}$$

where $\rho$ represents the probability of having a disease category given patient demographics, presence of certain therapeutic drug classes, and provider specialty information. The equation then is linearized via the logit transformation.

$$p' = \log_e\left(\frac{\rho}{1-\rho}\right) \quad \text{(Eq. 3)}$$

By performing the logit transform on both sides of the logit regression equation stated earlier, the standard linear regression model can be obtained:

$$p' = b_0 + b_1 x_1 + b_2 x_2 + \ldots + b_n x_n \quad \text{(Eq. 4)}$$

Via several SAS® macro programs, the modeling process examines therapeutic drug classes and provider specialty information listed in two lookup tables for each disease category it models and then selects relatively important drug categories and provider specialties as indicators. In one embodiment, a backward selection method is used in combination with various RIDGING methods for the modeling. In another embodiment, a forward selection method is used in combination with various RIDGING methods for the modeling. In one embodiment, a final model is generated by selecting only indicators having an effect at or above a specified alpha level. For example, in one embodiment, only those independent variables having an alpha level of 0.10 or greater are selected in the final model. The modeling process generates a mathematic model for each disease category and saves it into a model database.

Two exemplary models are provided below. It will be apparent to one of ordinary skill in the art that as more becomes known about certain conditions, drugs or their interaction that the indicators and associated models can be modified to produce varying results. In the examples listed below, the condition is first listed, and then followed by a table containing a list of significant indicators and the corresponding regression model.

For instance, for the condition of hypertension, pharmaceutical indicators grouped by drug category are hypotensives, ace blocking type (group G9); calcium channel blocking agents (group G18); beta-adrenergic blocking agents (group G180); potassium sparing diuretics in combination (group G334); thiazide and related diuretics (group G331); hypotensives, vasodilators (group G6); and potassium replacement (group G30) The groups are represented by their variable code as used in the statistical model. Demographics of importance are age and gender. Provider related variables are unique provider count, unique specialty count, and provider specialty dummy variables. In one embodiment, there are three age-related dummy variables used in the modeling are listed below:

| | |
|---|---|
| A0018 | "1", if member's age is 18 or less; else "0." |
| A1945 | "1", if member's age is from 19-45; else "0." |
| A4699 | "1", if member's age is greater than 45; else "0." |

In each of the below models, the variable "C" represents the intercept, and the variables "B1" to "Bn" represent coefficients associated with each independent variable, which are determined using the logistic regression modeling process.

Examples of Generated Probability Models:

| Rx drugs | Demographics | Provider Specialties |
|---|---|---|
| Hypertension: | | |
| HYPOTENSIVES, ACE BLOCKING TYPE (G9) CALCIUM CHANNEL BLOCKING AGENTS (G18) BETA-ADRENERGIC BLOCKING AGENTS (G180) POTASSIUM SPARING DIURETICS IN COM (G334) THIAZIDE AND RELATED DIURETICS (G331) HYPOTENSIVES, VASODILATORS (G6) POTASSIUM REPLACEMENT (G30) | Age Gender (gender_f) | UNIQUE PROVIDER COUNT (PROVCT) INTERNIST (P04) CARDIOLOGIST (P25) |

Hypertension Probability Model

P(Hypertension) = (C + G9*B1 + G18*B2 + G180*B3 + G334*B4 + G331*B5 + G6*B6 + G30*B7 + A1945*B8 + A4699*B9 + age*B10 + gender_f*B11 + PROVCT*B12 + P04*B13 + P25*B14)

Eye Disorders:

| | | |
|---|---|---|
| OPHTHALMIC ANTIBIOTICS (G307) MIOTICS/OTHER INTRAOC. PRESSURE RE (G297) EYE ANTIBIOTIC-CORTICOID COMBINATION (G299) ANTIHISTAMINES (G493) EYE ANTI-INFLAMMATORY AGENTS (G301) EYE SULFONAMIDES (G303) EYE ANTIHISTAMINES (G302) | Age Gender (gender_f) | UNIQUE PROVIDER COUNT (PROVCT) ALLERGIST (P02) INTERNIST (P04) OPHTHALMOLOGY (P08) OTOLARYNGOLOGY (P10) PEDIATRICIAN (P12) OPTOMETRIST (P22) |

Eye Disorders Probability Model

P(Eye Disorders) = (C + G307*B1 + G297*B2 + G299*B3 + G493*B4 + G301*B5 + G303*B6 + G302*B7 + A1945*B8 + A4699*B9 + age*B10 + gender_f*B11 + PROVCT*B12 + P02*B13 + P04*B14 + P08*B15 + P10*B16 + P12*B17 + P22*B18)

Exemplary User Interface

Figure 2:
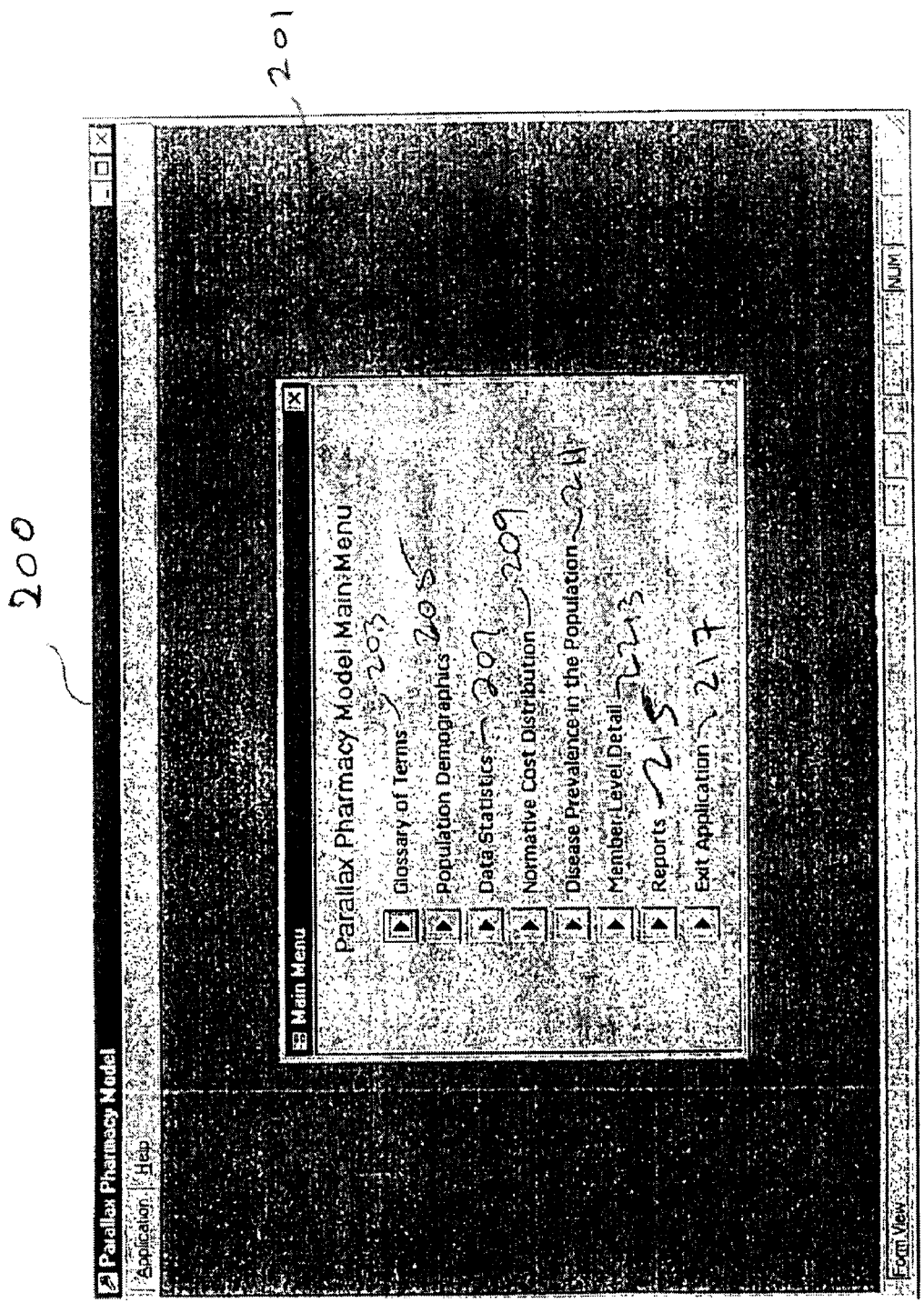
FIG. 2 is a screen shot for a main menu in an exemplary GUI, according to the present system and method.

FIG. 2 shows an exemplary user interface for a pharmacy model software application. Display window 200 shows a parallax pharmacy model, in run time mode. In one embodiment, the exemplary model uses a Microsoft® Access database. Display window 201 is a main menu for this model. There are a number of buttons corresponding to the number of functions available in the model. In the exemplary model, top level functions available are: glossary of terms 203; population demographics 205; data statistics 207; normative cross distribution 209; disease prevalence in the population 211; member detail 213; reports 215; and an option to exit the application 217.

The software application shown in FIGS. 2-18 incorporates the modeling techniques described above and generates reports to help an administrator of a risk-based health plan to manage the health of the plan members and the plan costs. For example, as further described below the software application assists the administrator in identifying a course of action for performing intervention for one or more plan members, educating one or more members, or encouraging treatment for one or more members.

Figure 3:
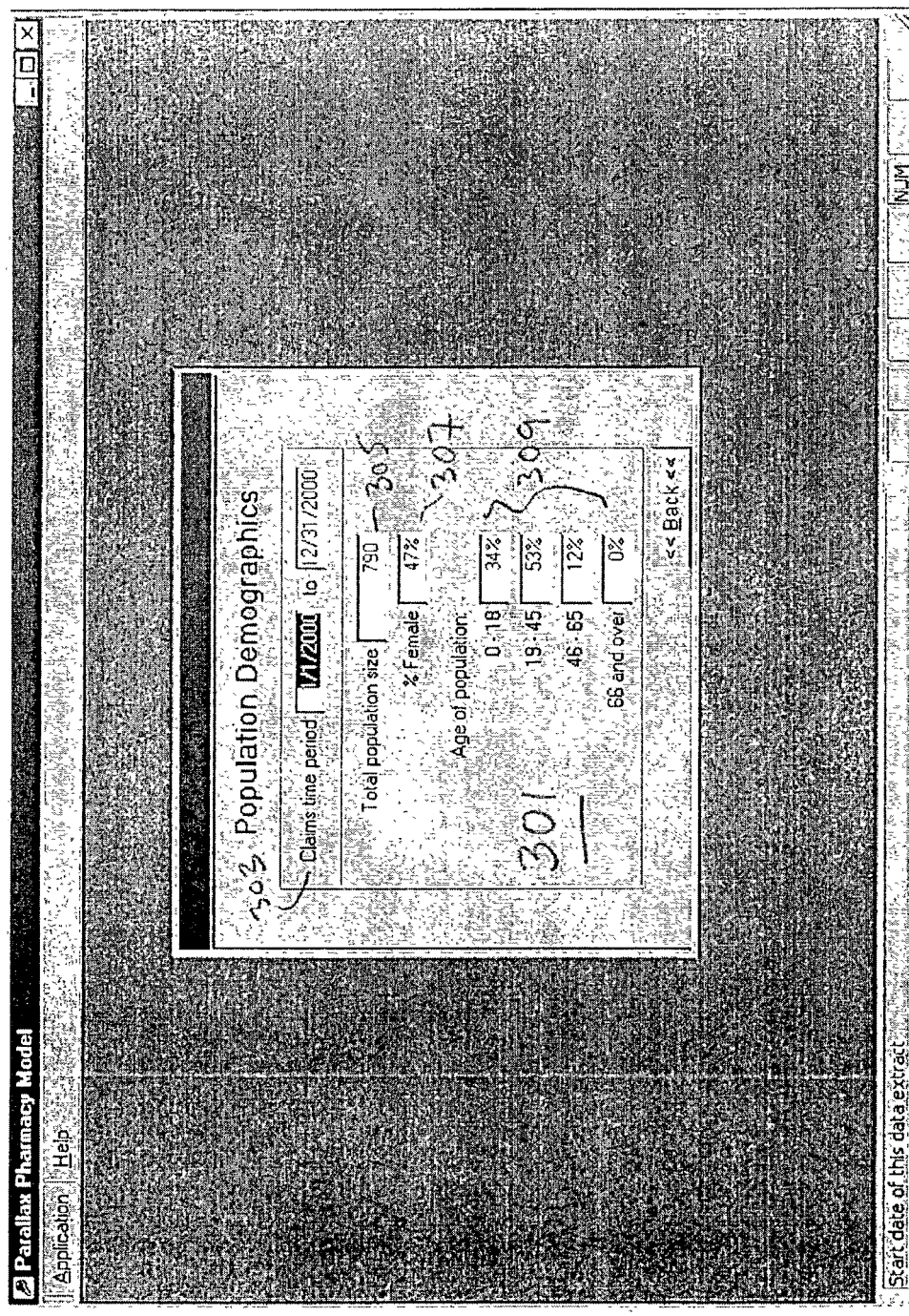
FIG. 3 is a screen shot for a population demographics screen in an exemplary GUI, according to the present system and method.

FIG. 3 shows a user interface window 303 for the population demographics function. The population demographics window 301 shows data from the database for which the model is based. For instance, the time period from which the claims are selected is shown at 303. The total population size is shown at 305. The percent female is shown at 307. It will be apparent to one of ordinary skill in the art that the percent of male members of the demographics could have been shown in the alternative. The age of the population is also shown at 309. In the exemplary model, the age brackets selected are ages 0-18, 19-45, and 46-99. It will be apparent to one of ordinary skill in the art that different age brackets may be used if the statistical analysis warrants.

Figure 4:
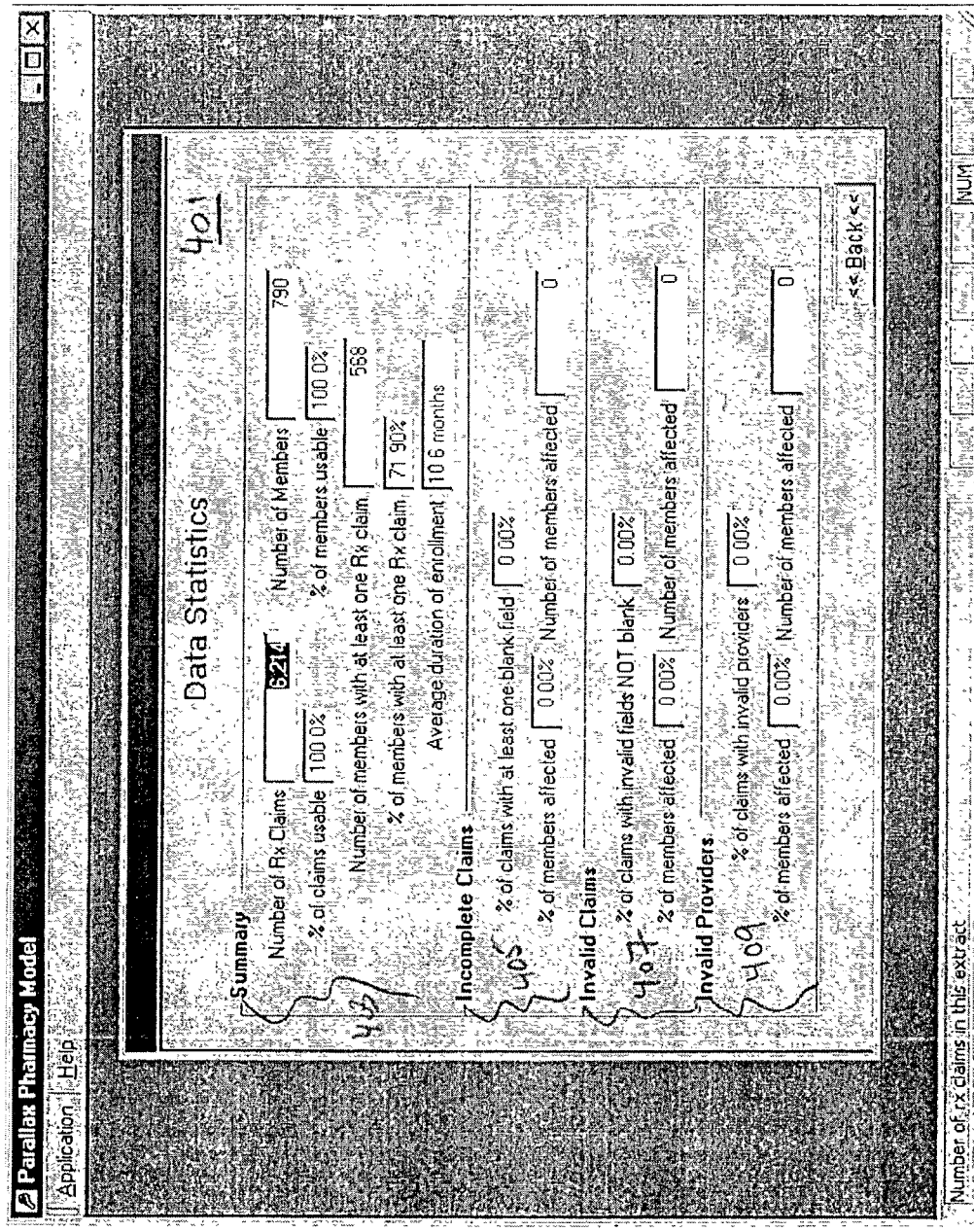
FIG. 4 is a screen shot for a data statistics screen in an exemplary GUI, according to the present system and method.

FIG. 4 shows a data statistics window 401. The data statistics window shows statistical data relevant to the model and the population. For instance, the data statistics window shows a summary section 403 having information listed for the number of Rx claims, the number of members, the percent of usable claims, the percent of usable members, the number of members with at least one Rx claim, the percent of members with at least one Rx claim and average duration of enrollment. The data statistics window 401 also shows a section for incomplete claims 405, which shows the percent of claims with at least one blank field, the percent of members affected and the number of members affected. The window also shows a section for invalid claims 407 having information for the percent of claims with invalid fields not blank, the percent of members affected, and the number of members affected. The data statistics window also has a section for invalid providers 409, which shows information for percent of claims with invalid providers, percent of members affected and the number of members affected. This data is shown merely to assist the user in determining the validity and viability of the results of the model.

FIG. 5 shows the normative cost distribution window 501. The exemplary normative cost distribution window has a table with three columns: the first column is the disease category; the second column is the per member per month ("PMPM") dollars; and the thirds column is the percent of total PMPM; for instance, the first row of the table 503 shows a disease category of pregnancy. The PMPM dollars is $1327, and the percent of total is 11%. The user can sort the disease categories or the percent total by any of the headers. In other words, the disease categories can be sorted alphabetically, or the user may wish to view by percent of total and sort these in ascending or descending order by clicking on the header of the column.

The Disease Cost is the cost associated with management of a condition representing the cumulative experience in a normative population. It is divided into facility, outpatient and drug costs. A normative population is a population made of randomly pooled members from a set of national health plans. This population is expected to represent the national healthcare experience.

FIG. 6 shows the window "disease prevalence in the population" 601. Prevalence in a population is the estimated occurrence of an attribute of a population expressed typically as a percentage or a number per 1000 population. Examples of attributes include disease (asthma, diabetes), event (hospitalization, stroke), etc. The data in this table is useful, because it allows a user to determine an estimated or predicted member count as opposed to the prevalence in the current population for a certain condition or disease. The disease prevalence in population menu screen 601 shows a table with six columns: the first column is the disease or condition category; the second column is the predicted member count; the third column is the prevalence in current population; the fourth column is prevalence point difference; the fifth column is the prevalence in normative population; and the last column, is the percent of total cost.

For instance, in this exemplary data base, the population shows that, for acute or unspecified arthropathies and minor tendon disorders, the predicted member count is 24. The prevalence in the current population is 3%, and the percent of total cost is 1%. These columns can be sorted by selecting the header for the particular column. Thus, the user may wish to view the disease categories alphabetically or view the predicted member counts or percent of total cost to determine which conditions are most likely to occur in the population or which conditions are likely to cost the most amount of money. The total cost for the past year is also displayed. In addition to seeing statistics for the population as a whole, statistics based on each member of the population are accessible.

Figure 7:
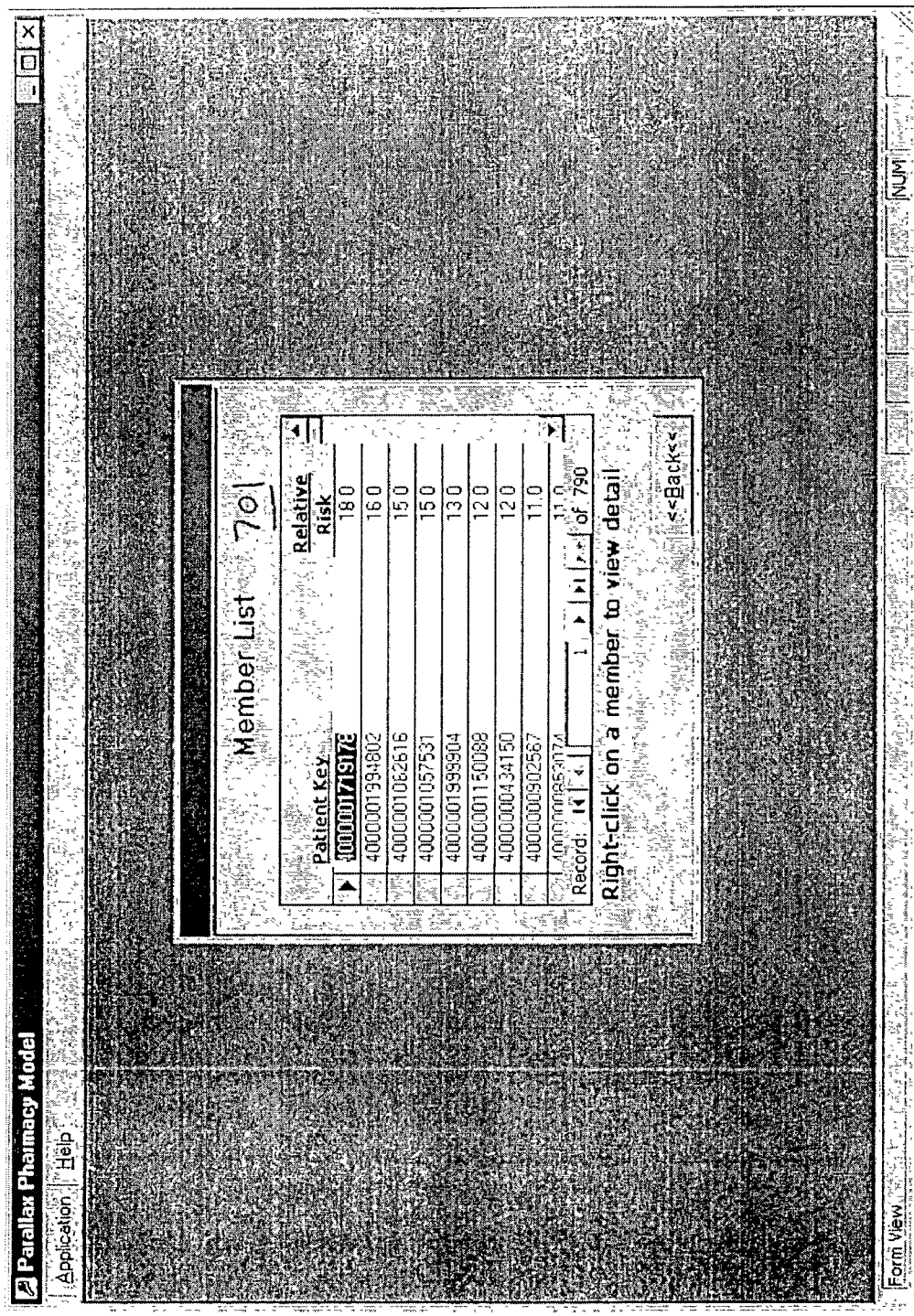
FIG. 7 is a screen shot for a member list screen in an exemplary GUI, according to the present system and method.

FIG. 7 shows an exemplary display for the member list of the current population 701. The member list window 701 has two columns of information: the first, is the patient key; and the second, is the relative risk. Relative risk is the estimated resource consumption of a member in a future time period expressed relative to a baseline. An example of a baseline could be the mean cost of a health plan member in a prior year. The patient keys can be indexed to correspond to individual people or, in some cases, if required by law or privacy rules and policies, can be anonymous. For some embodiments of the present invention, being able to identify individuals by name may be useful for predicting and avoiding risks for conditions and diseases. If the users select a specific patient key from the member list in window 701, an additional detail menu, 801 of FIG. 8, is displayed.

Figure 8:
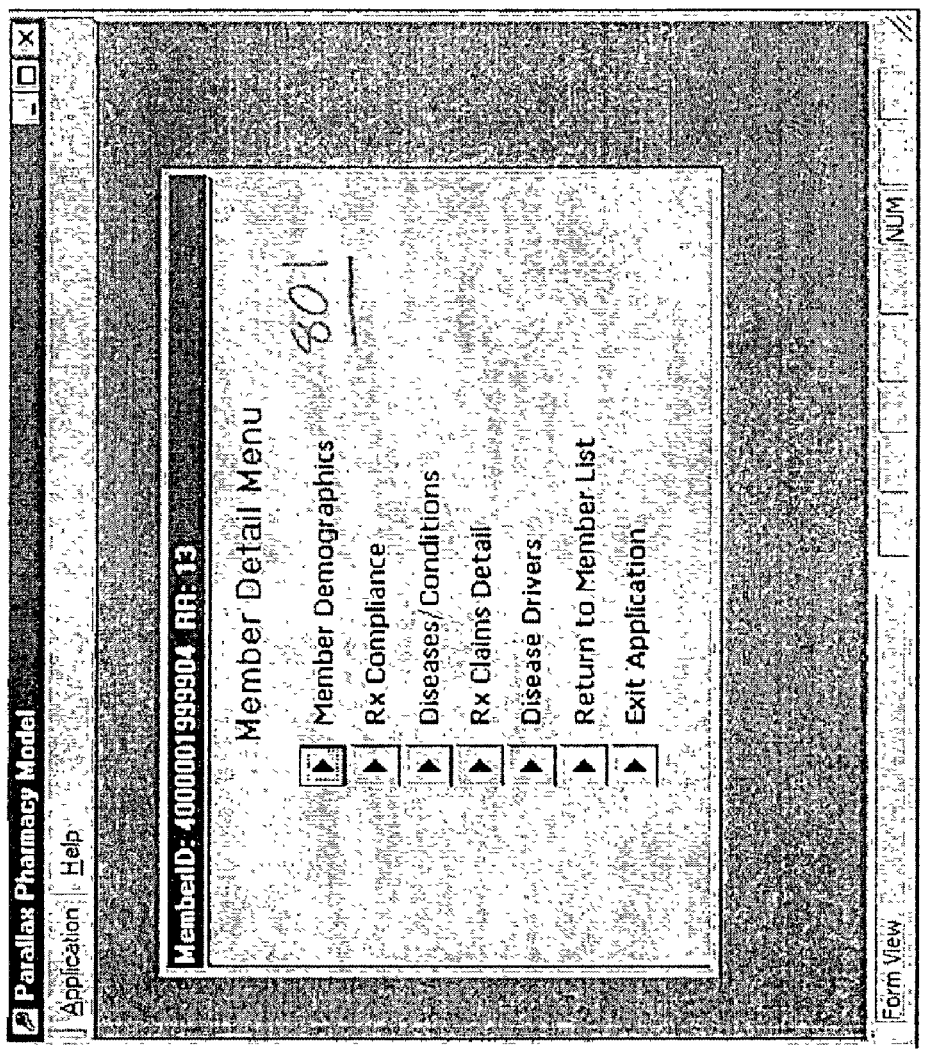
FIG. 8 is a screen shot for a member detail menu screen in an exemplary GUI, according to the present system and method.
Figure 9:
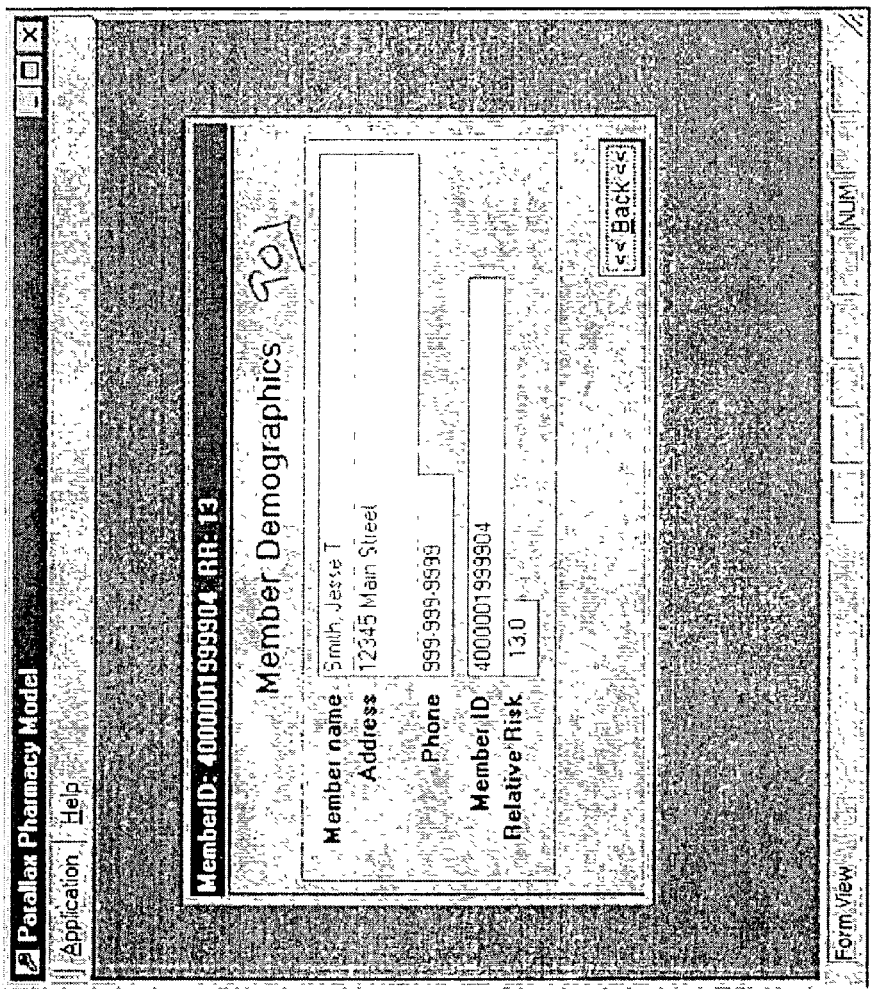
FIG. 9 is a screen shot for a member demographics screen in an exemplary GUI, according to the present system and method.

FIG. 8 shows the member detail menu 801. The member detail menu 801 has several selectable items which will display further information; for instance, in the exemplary menu, member demographics, Rx compliance, diseases/conditions, Rx claims detail, and diseases drivers can all be displayed. Rx compliance is also referred to as drug possession ratio. It measures the frequency of actual fill of a drug category (e.g. oral hypoglycemics, anti-migraine medication, etc) prescription relative to the expected frequency. The user is also given the option to return to the member list to select a different member or to exit the application. The member demographics screen, as shown in FIG. 9, has a number of data specific to the member. The member demographics window 901 displays the member name, address and phone number, as well as the member I.D. and the relative risk. In this way, certain members who are high risk can be contacted or targeted for specific disease avoidance methods.

Figure 10:
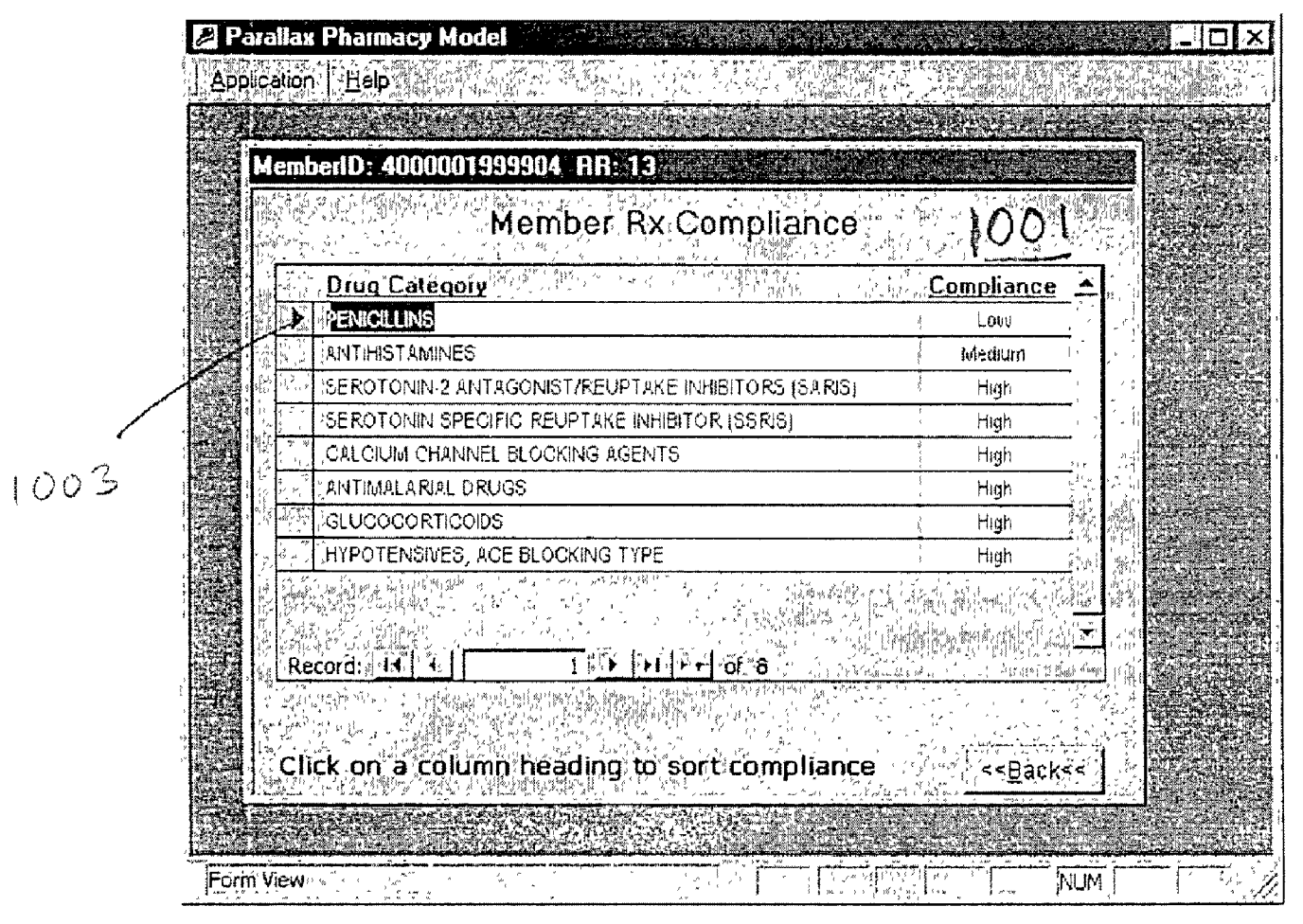

FIG. 10 shows an exemplary display window showing member Rx compliance. The Rx compliance window 1001 shows the drug category and the compliance level for the selected member. For instance, the first row of the exemplary table shows penicillin 1003, and the compliance level of low. This shows that, based on the member's prescription, the days of supply, and the frequency of refilling that supply, that the member is not likely to be taking the drug at the prescribed level.

Figure 11:
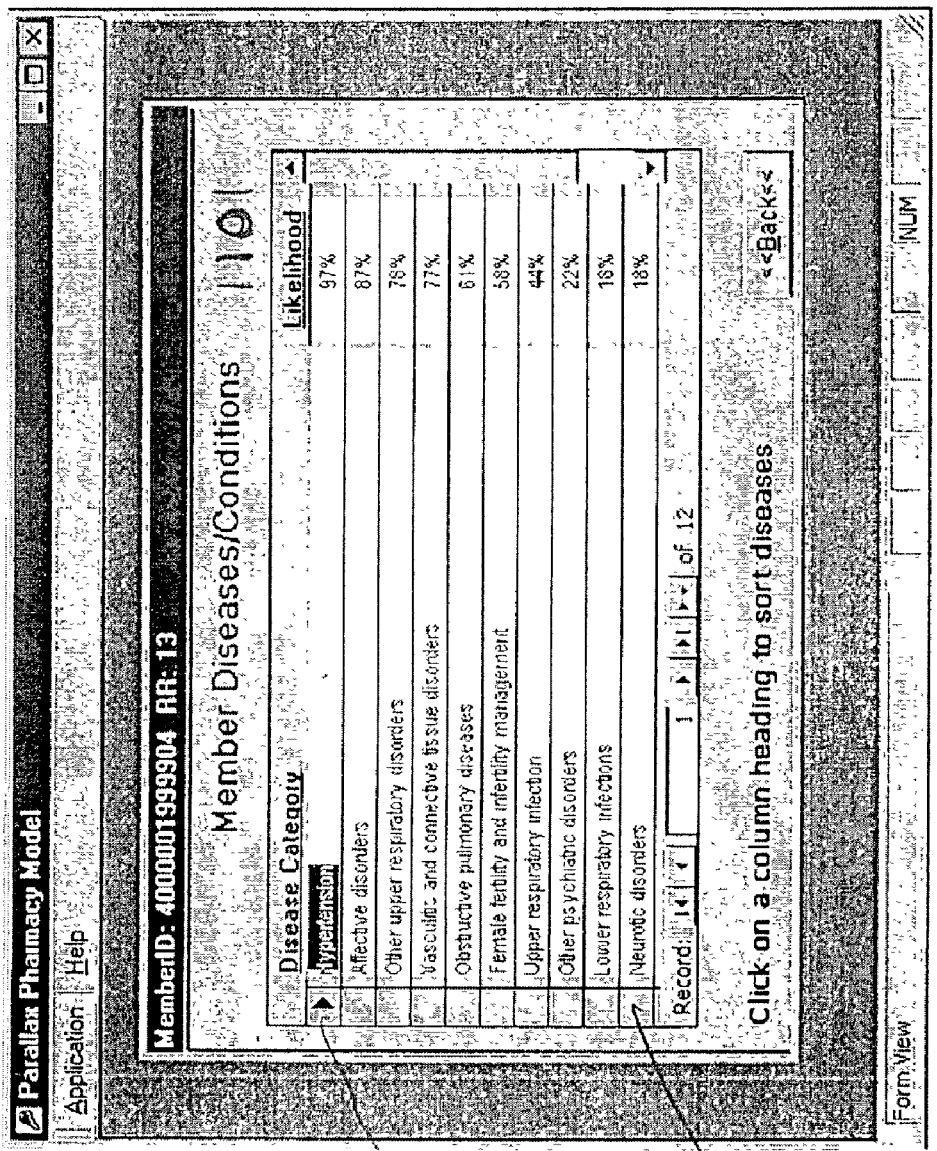
FIG. 11 is a screen shot for a member diseases/conditions screen in an exemplary GUI, according to the present system and method.

FIG. 11 shows an exemplary window for member diseases and conditions 1101. For instance, in this exemplary window, a disease category is shown for a selected member with a likelihood that member has this disease. A Disease Likelihood is an estimate of the frequency of presence of a disease given the specific attributes of the patient. For example, given that a patient is managed with insulin and oral hypoglycemics, the likelihood is 0.6 that the patient has diabetes.

In this exemplary window, for a selected member, it is shown that this particular member has a 97% likelihood of hypertension, in the first row 1003, and that this member has only an 18% likelihood of having a neurotic disorder, as shown in the last row of the display window 1105. As with the other exemplary windows, the diseases or the likelihood columns can be sorted in ascending or descending order by clicking on the header for that particular column.

FIG. 12 shows an exemplary window for the member Rx claim detail. The member Rx claims detail window 1201 shows, for a selected member, each drug that member has filled for the selected time period. In this exemplary window, there are columns for the drug category, the drug name, the NDC code, the date filled, the amount paid and the days supply. In this example, the member has been prescribed and filled medications for contraceptives, selective seratonin reuptake inhibitors, calcium channel blocking agents, antimalarial drugs, glucocorticoids, etc. It can be seen that this particular member filled a prescription for seratonin on Jan. 14, 2000, at line 1203, and also filled a prescription for the same substance on Feb. 14, 2000, at line 1205. In both cases, a 30 days' supply was given, and it can also be seen that these prescriptions were filled 30 days apart. Referring again to FIG. 10, it can be seen on the member Rx compliance window 1001, that this particular member's compliance rate for the seratonin is high, corresponding to that member filling the prescriptions in time to continue to take the drug for the prescribed amount.

FIG. 13 shows a member disease drivers screen 1301, for a selected member. There are two columns in the exemplary screen. The disease category 1303 is shown in column one. The disease driver rank 1305 is shown in column two. The disease driver rank shows the relative risk of diseases and conditions for a selected member. The Disease Rank is a scheme to enable directed health care interventions in a member. The rank associated with a disease in a member enables prioritization for intervention purposes. In the exemplary screen 1301, it is shown that for the selected member, affective disorders is the highest ranked disease, whereas, upper respiratory infection is ranked at 10. Thus, it can be seen that for the selected member, affected disorders will be a more costly condition.

Figure 14:
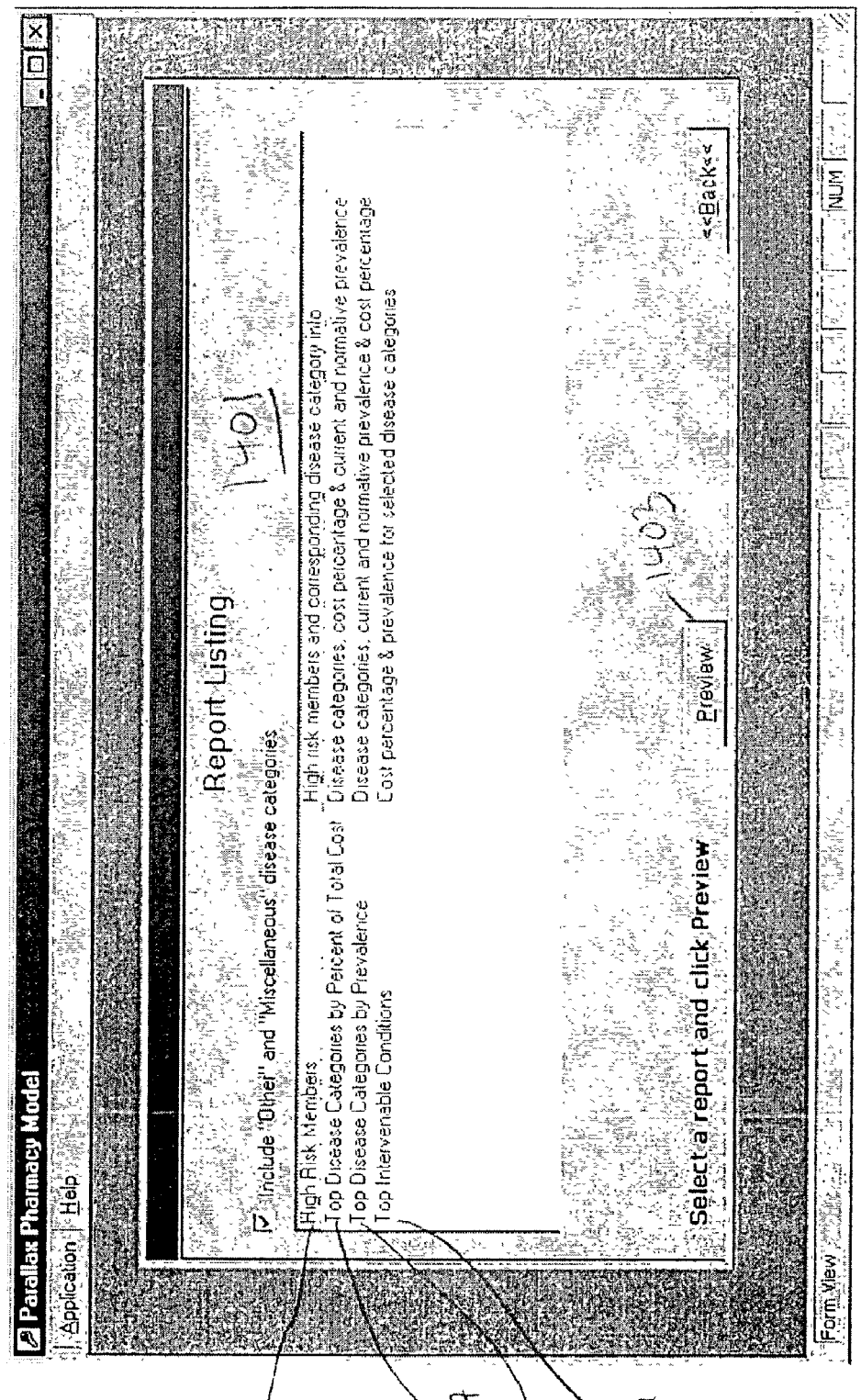
FIG. 14 is a screen shot for a data statistics screen in an exemplary GUI, according to the present system and method report listing menu screen in an exemplary GUI, according to the present system and method.

The exemplary model allows for several different reports to be run, based on the user's interest. FIG. 14 shows a report listing display screen 1401, with a list of the types of reports that can be run in one embodiment. The user can run the report by clicking and highlighting on it and previewing the report by clicking on the preview button 1403. In one embodiment, the report is printed from the preview screen. It will be apparent to one of ordinary skill in the art that any number of reports can be generated based on the data provided by the models, and it can be presented to the user in a variety of ways. The first report type that can be generated is a list of high risk members report 1405. This report lists the high risk members and their corresponding disease category information. This information is useful for taking proactive avoidance action.

The next report type which is available is the "top diseases" categories by percent of total cost report 1407. This report shows the disease category, cost percentage and current and normative prevalence. The next report available is "top disease categories by prevalence"; report 1409. This report shows disease categories, current and normative prevalence and cost percentage. The results of these reports 1407 and 1409 can be used by a health care plan administrator to help identify disease categories which are driving plan costs. The administrator can then focus on methods for reducing costs in these categories. The fourth report type available is "top intervenable conditions"; report 1411. This report shows the cost percentage and prevalence for selected disease categories. This report is useful for either an employer or health care organization to find out which diseases can be most avoided. For instance, if diabetes was a high risk for many members of the population and it can be intervened by providing courses and seminars on proper eating habits and proper insulin taking skills, or the such, it might be useful for an employer to provide such classes for the employees to reduce its total health costs.

Figure 15:
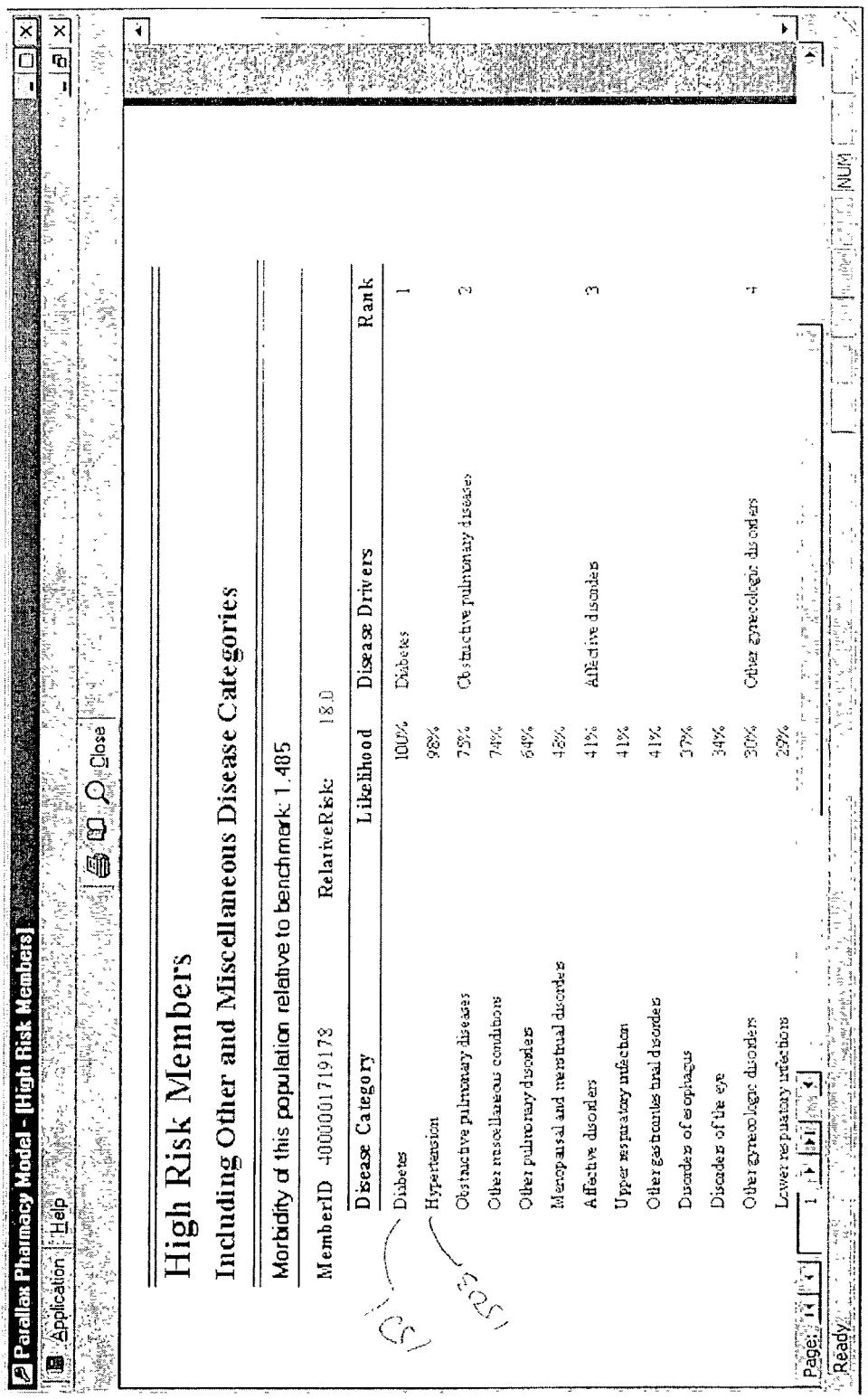
FIGS. 15, 16, 17, and 18 show exemplary reports generated according to the present system and method.

FIGS. 15, 16, 17 and 18 show exemplary reports as provided in the model. FIG. 15 shows a report for high risk members. It can be seen from this report that, for this selected member, the relative risk is 18. The disease category likelihood and disease drivers are also shown; for instance, for diabetes, in line 1501, the likelihood for this particular member is 100%. The disease driver for this, is diabetes, and the rank is 1. The likelihood for hypertension 1503 is 98%. Thus, it could be seen, for this particular member, courses in diabetes control and in reducing blood pressure might be helpful to reduce overall health costs.

Figure 16:
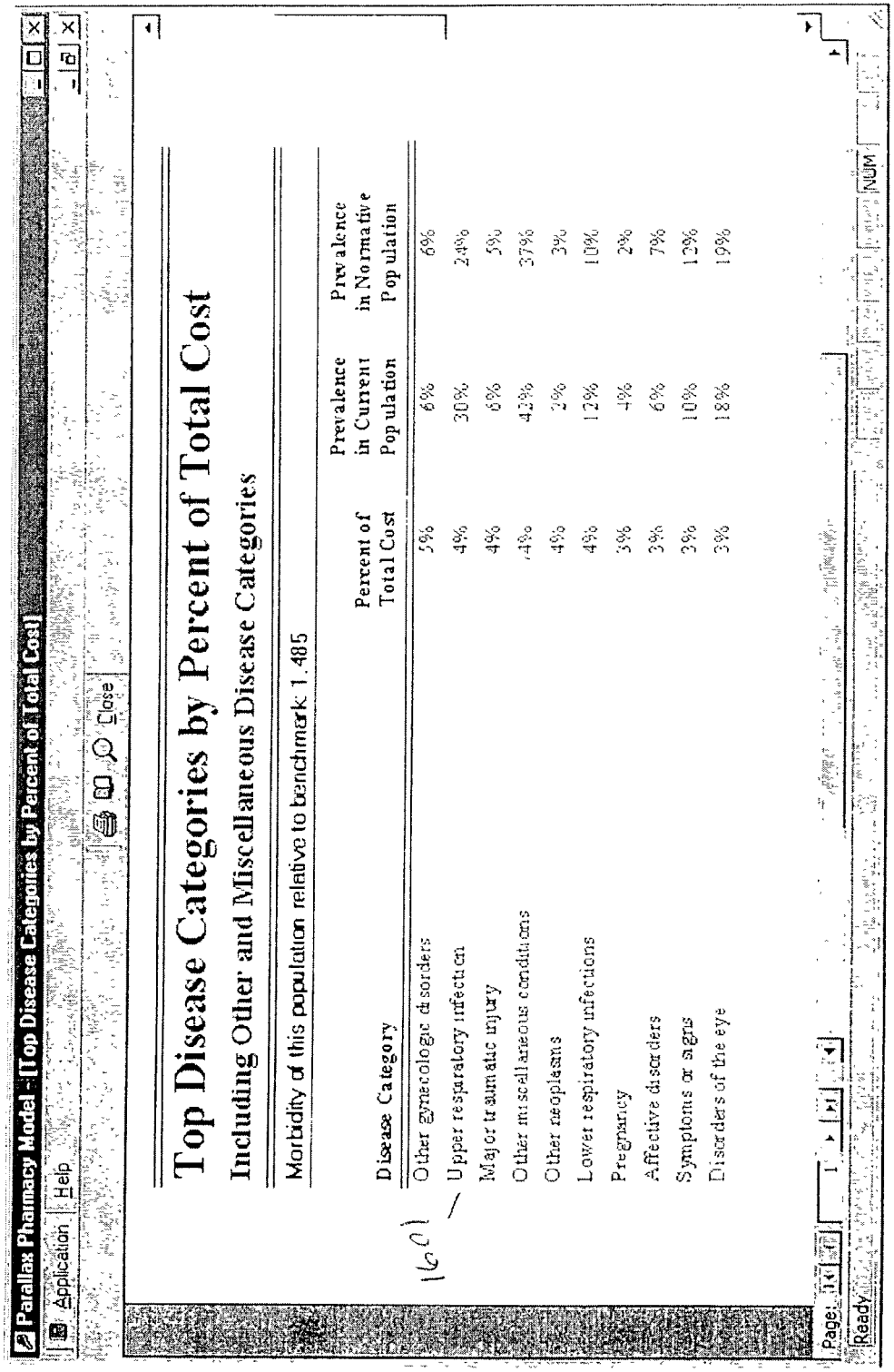

FIG. 16 shows a report for its top disease categories by percent of total cost. For instance, this report shows that for the general population of this model, upper respiratory infections are 4% of the total cost, and their prevalence in this current population is 30%. The prevalence in the normative population for upper respiratory infection, 1601, is only 24%. Thus, it can be seen that the current population has a higher incidence of upper respiratory infections, as compared to the normal population. Thus, certain preventative measures or seminars in preventing this type of infection might be worthwhile to reduce overall costs.

Figure 17:
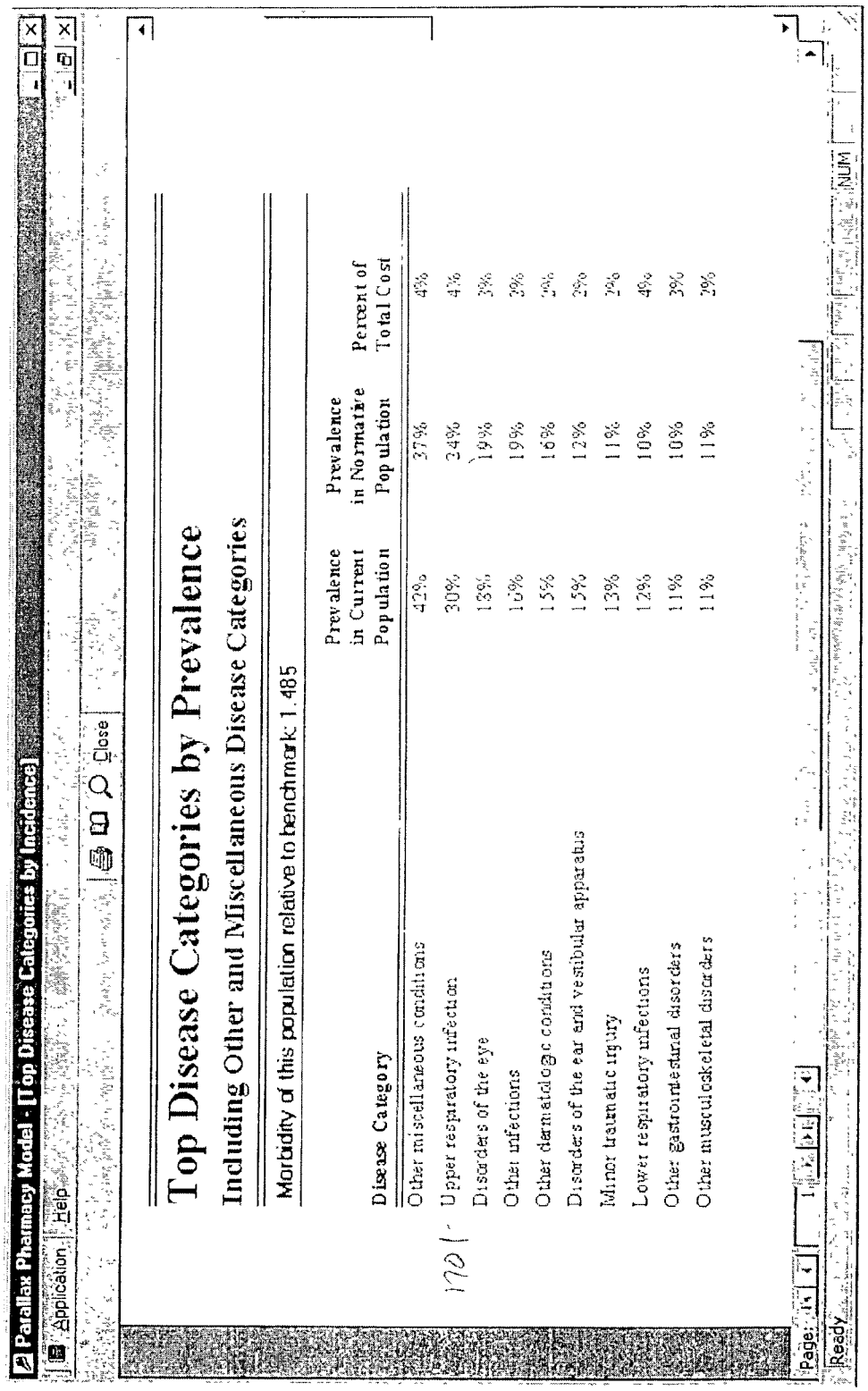

FIG. 17 shows an exemplary report for top disease categories by prevalence. For instance, for the disease category "upper respiratory infection," 1701, it is seen that the prevalence in the current population is 30%, the prevalence in the normative population is 24%, and the percent of total cost is 4%. This is the same data as shown in the report shown in FIG. 16; however, the categories are put in different columns and may be visually more aesthetic, depending on the information required by the user.

Figure 18:
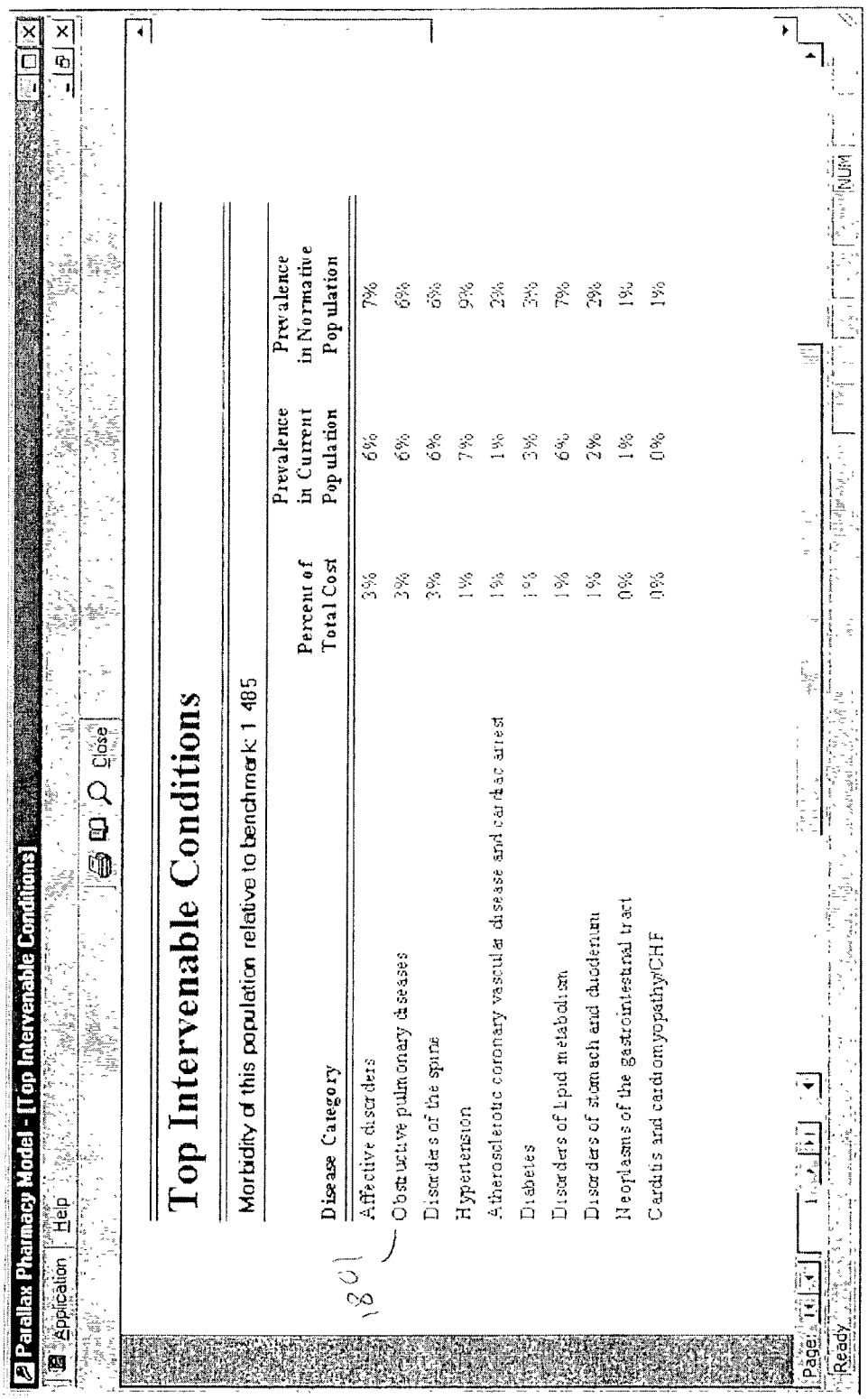

FIG. 18 shows a report for the top intervenable conditions for this population. For instance, obstructive pulmonary diseases, 1801, is shown to be 3% of the total cost, 6% prevalence in the current population, and also 6% prevalence in the normative population.

The present invention has several potential applications relating to managing healthcare outcomes. For example, the information provided by the application can be used to track and manage health care plan costs, to manage drug compliance, and to facilitate disease management. Once non-compliance or the presence of a disease category is determined, an employer or a health care plan can intervene in the member's care to attempt to improve outcomes, by providing education to the member or by encouraging treatments.

Other Applications of the Probability Modeling System

Another application of the present invention is life insurance underwriting. The modeling process can be used to facilitate accurate and more efficient underwriting of life insurance applications. A life insurance company intending to underwrite an individual can specify a set of conditions or disease categories of interest and use the models of the present invention to determine the probability of these disease categories for a person seeking life insurance coverage. As discussed above, the disease categories of interest are those relevant to the longevity or mortality of the member. A decision on whether to offer coverage and, if so, at what premium is then made depending on these probabilities. For example, in one embodiment, an adjustment is made from a base premium, based on these probabilities. A sample life insurance underwriting system that could be used with the models of the present invention is disclosed in co-pending U.S. patent application Ser. No. 09/596,810, filed Jun. 19, 2000, entitled "Method and Apparatus for Requesting and Retrieving Medical Information," which is hereby incorporated by reference in its entirety.

Another application of the present invention is health insurance underwriting based on pharmacy claims for a member or for a set of members. In this application, the models of the present invention are used in conjunction with a model for predicting future health resource consumption and to estimate the probability of conditions or disease categories of interest to a health insurance underwriter. This information is then used to appropriately rate individual and group insurance policies. In one embodiment, the probability models of the present invention are used in conjunction with a predictive model of the type disclosed in co-pending U.S. patent application Ser. No. 09/635,911, as described above.

In another embodiment, the present invention is used by CMS, to facilitate incorporating managed care companies into the senior care system. Until recently, CMS paid the managed care plan for health care of senior enrollees based only on an age and gender rating. CMS has expressed a desire to move towards risk-based reimbursement, based on the presence of conditions it specifies. The present invention enables this risk-based reimbursement by determining a probability that a member or a set of members have one or more of these specified conditions, based solely on an analysis of pharmacy claims. These probabilities are used by an administrator of the plan to identify members that likely have a condition of interest and to follow up with the members physician to verify the condition and to obtain proper documentation.

Exemplary Probability Modeling System

Figure 19:
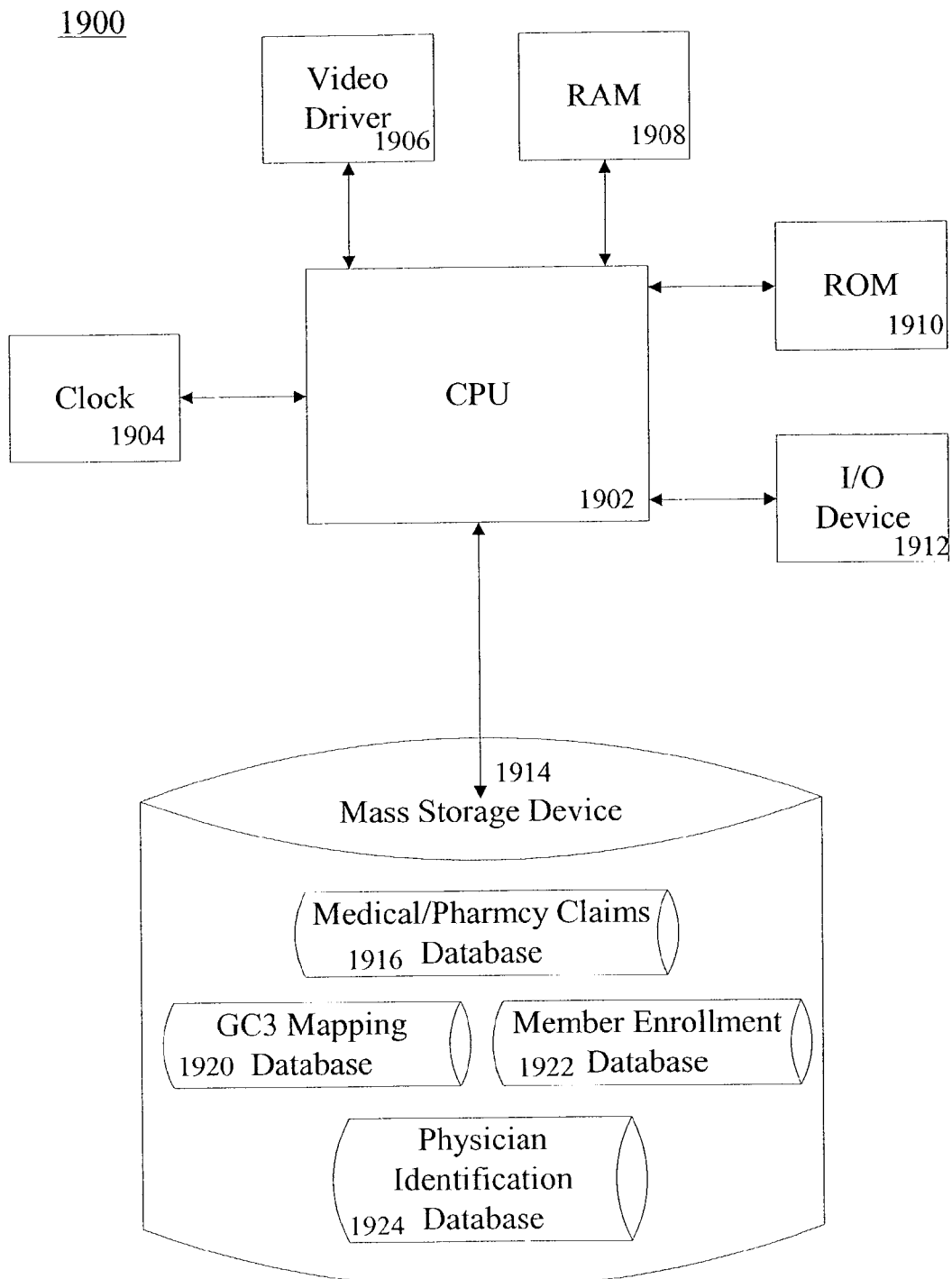
FIG. 19 shows a block diagram of a disease category probability modeling system, according to one embodiment of the present invention.

FIG. 19 shows a block diagram of a disease category probability modeling system 1900 according to one embodiment of the present invention. As shown in FIG. 19, the modeling system 1900 includes a central processing unit (CPU) 1902, a clock 1904, a video driver 1906, a random-access memory (RAM) 1908, a read-only memory (ROM) 1910, an input/output (I/O) device 1912, and a mass storage device 1914. The clock 1904, the video driver 1906, the RAM 1908, the ROM 1910, the I/O device 1912, and the mass storage device 1914 are all in two-way communication with the CPU 1902.

In one embodiment, the video driver 1906 is coupled to a display device (not shown) for displaying the results generated by the modeling system 1900. In another embodiment of the present invention, no display device is included. The I/O device 1912 allows the CPU 1902 to exchange information with an external source (not shown). For example, in one embodiment, the CPU 1902 connects with an external database containing information needed for the modeling process (e.g., a GC3 mapping database, a DEA or other physician identification database, or a member enrollment information database). In one embodiment, the I/O device 1912 is coupled to a keyboard, which allows an operator to initiate the system or modify certain parameters. In another embodiment, the I/O device 1912 is connected to another computer system or to a network such as the Internet, which allows the CPU 1902 to cause results generated by the modeling system 1900 to be sent to another system for viewing or further processing.

The mass storage device 1914, in one embodiment, contains a medical/pharmacy claims database 1916, a GC3 mapping database 1920, a member enrollment database 1922, and a physician identification database 1924. In one embodiment, the mass storage device 1914 does not contain a full medical and pharmacy claims database, but instead includes only a pharmacy claims database. In other embodiments, the mass storage device 1914 contains other data sets, as needed to carry out the modeling method 10, as described above. In one embodiment, the mass storage device 1914 does not include any of the databases identified above, but instead the necessary information is obtained from one or more external databases.

During operation of the modeling system 1900, the CPU 1902 executes code, located in the RAM 1908 and the ROM 1910, instructing the CPU 1902 to carry out the methodology of the modeling method 10. The CPU 1902 then executes the code, at a processing rate controlled by the clock 1904. The CPU 1902 draws the data necessary to perform the modeling method 10 either from files in the mass storage device 1914 or by prompting the operator for input through the I/O device 1914. Once the CPU 1902 has all necessary information, it constructs a model for each specified disease category, computes a probability, and outputs the results. The results can either be sent through the video driver 1906 to a display device, such as a video monitor or a printer, or sent out to another system through the I/O device 1912.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. Although the present invention has been described with reference to exemplary embodiments, persons skilled in the art will recognize that changes may be made in form and detail without departing from the spirit and scope of the invention.

We claim:

1. A computer-implemented method for determining the probability of the presence of each of a plurality of disease categories for at least one patient, comprising:

storing in at least one electronic database:
pharmacy claim data for at least one patient;
a plurality of drug classes, each including one or more associated drug codes;
a plurality of provider specialty categories, each including one or more associated provider specialties;
a plurality of disease categories, wherein each disease category is associated with at least one disease or health-related condition; and
a plurality of probability equations, one for each stored disease category, wherein each probability equation may be used to calculate a probability that a patient has a specific disease category based upon presence of drug classes and provider specialties in the patient's pharmacy data;
for each patient, using a computer processor to assign a first set of variables comprising one variable for each stored drug class, wherein each assigned variable in the first set of variables indicates the presence or absence of at least one drug code associated with the stored drug class in the patient's pharmacy claim data;
for each patient, using the computer processor to assign a second set of variables comprising one variable for each stored provider specialty category, wherein each assigned variable in the second set of variables indicates the presence or absence of a provider specialty associated with the stored provider specialty category in the patient's pharmacy claim data;
storing the first and second sets of variables for each patient in a data record in the at least one electronic database;
using the computer processor to calculate a disease probability value for each patient for each disease category using the respective stored probability equation for the disease category and data from the patient's data record; and
storing the calculated disease probability values in each patient's data record in the at least one electronic database.

2. The computer-implemented method according to claim 1, wherein the calculated probability values for a patient are used to determine a premium for an insurance policy covering the patient.

3. The computer-implemented method according to claim 2, wherein the insurance policy is a life insurance policy.

4. The computer-implemented method according to claim 2, wherein the insurance policy is a health insurance policy.

5. The computer-implemented method according to claim 1, further comprising automatically generating a report containing data from at least one patient's data record.

6. The computer-implemented method according to claim 5, wherein the report is displayed on a user interface.

7. The computer-implemented method according to claim 1, wherein the disease categories are Clinical Care Group (CCG) categories.

8. The computer-implemented method according to claim 1, wherein the drug classes are therapeutic drug classes.

9. The computer-implemented method according to claim 1, wherein the first set of variables for each patient comprises "0" and "1" variables, wherein "0" indicates an absence of a drug code associated with the stored drug class, and "1" indicates the presence of a drug code associated with the stored drug class.

10. The computer-implemented method according to claim 1, wherein the second set of variables for each patient comprises "0" and "1" variables, wherein "0" indicates an absence of a provider specialty associated with the stored provider specialty category and "1" indicates the presence of a provider specialty associated with the stored provider specialty category.

11. The computer-implemented method according to claim 1, wherein the disease probability value for each patient for each disease category is further calculated using one or more aggregate factors for each patient, wherein the aggregate factors include a number of unique providers for the patient, a number of unique drug categories for the patient, and a number of unique provider specialties for the patient.

12. The computer-implemented method according to claim 1, wherein the disease probability value for each patient for each disease category is further calculated using demographic data for the patient.

* * * * *